US012788748B2

(12) United States Patent
Parkin

(10) Patent No.: US 12,788,748 B2
(45) Date of Patent: Nov. 10, 2026

(54) METHODS INVOLVING NEUTROPHIL ELASTASE INHIBITOR ALVELESTAT FOR TREATING RESPIRATORY DISEASE MEDIATED BY ALPHA-1 ANTITRYPSIN DEFICIENCY

(71) Applicant: MEREO BIOPHARMA 4 LIMITED, London (GB)

(72) Inventor: Jacqueline Parkin, London (GB)

(73) Assignee: MEREO BIOPHARMA 4 LIMITED, London (GB)

( * ) Notice: Subject to any disclaimer, the term of this patent is extended or adjusted under 35 U.S.C. 154(b) by 909 days.

(21) Appl. No.: 17/995,909

(22) PCT Filed: Mar. 16, 2021

(86) PCT No.: PCT/GB2021/050653

§ 371 (c)(1),
(2) Date: Oct. 10, 2022

(87) PCT Pub. No.: WO2021/209739

PCT Pub. Date: Oct. 21, 2021

(65) Prior Publication Data

US 2023/0190723 A1 Jun. 22, 2023

Related U.S. Application Data

(60) Provisional application No. 62/706,195, filed on Aug. 4, 2020.

(30) Foreign Application Priority Data

Apr. 16, 2020 (GB) ..................................... 2005519
Apr. 16, 2020 (GB) ..................................... 2005520

(51) Int. Cl.

*A61K 31/444* (2006.01)
*A61K 45/06* (2006.01)
*A61P 11/00* (2006.01)
*A61P 31/14* (2006.01)

(52) U.S. Cl.

CPC ............ *A61K 31/444* (2013.01); *A61K 45/06* (2013.01); *A61P 11/00* (2018.01); *A61P 31/14* (2018.01)

(58) Field of Classification Search

CPC ........... A61P 11/00; A61P 29/00; A61P 31/14; A61K 31/444; A61K 45/06

See application file for complete search history.

(56) References Cited

U.S. PATENT DOCUMENTS

| | | | | |
|---|---|---|---|---|
| 10,960,062 | B2 * | 3/2021 | Tov | A61K 38/57 |
| 2022/0354833 | A1 | 11/2022 | Parkin et al. | |
| 2023/0218596 | A1 | 7/2023 | Parkin et al. | |

FOREIGN PATENT DOCUMENTS

| | | | |
|---|---|---|---|
| WO | WO199215605 | A2 | 9/1992 |
| WO | WO199220357 | A1 | 11/1992 |
| WO | WO199311760 | A1 | 6/1993 |
| WO | WO199321209 | A1 | 10/1993 |
| WO | WO199321210 | A1 | 10/1993 |
| WO | WO199321212 | A1 | 10/1993 |
| WO | WO199321213 | A1 | 10/1993 |
| WO | WO199321214 | A1 | 10/1993 |
| WO | WO199324519 | A1 | 12/1993 |
| WO | WO199401455 | A1 | 1/1994 |
| WO | WO199527055 | A1 | 10/1995 |
| WO | WO199533762 | A1 | 12/1995 |
| WO | WO199533763 | A1 | 12/1995 |
| WO | WO199616080 | A1 | 5/1996 |
| WO | WO199623812 | A1 | 8/1996 |
| WO | WO199736903 | A1 | 10/1997 |
| WO | WO199739028 | A1 | 10/1997 |
| WO | WO199912931 | A1 | 3/1999 |
| WO | WO199912933 | A2 | 3/1999 |
| WO | WO199962514 | A1 | 12/1999 |
| WO | WO199962538 | A1 | 12/1999 |
| WO | WO2003031574 | A2 | 4/2003 |
| WO | WO2003058237 | A1 | 7/2003 |
| WO | WO2004020412 | A1 | 3/2004 |
| WO | WO2004043924 | A1 | 5/2004 |
| WO | WO2005021509 | A1 | 3/2005 |
| WO | WO2005021512 | A1 | 3/2005 |
| WO | WO2005026123 | A1 | 3/2005 |
| WO | WO2005026124 | A1 | 3/2005 |
| WO | WO2005082863 | A2 | 9/2005 |
| WO | WO2005082864 | A1 | 9/2005 |
| WO | WO2006070012 | A1 | 7/2006 |
| WO | WO2006082412 | A2 | 8/2006 |
| WO | WO2006098684 | A1 | 9/2006 |
| WO | WO2006136857 | A1 | 12/2006 |
| WO | WO2007107706 | A2 | 9/2007 |

(Continued)

OTHER PUBLICATIONS

NCT03679598 (National Library of Medicine, Clinical Trial.gov ID, Version 2, Sep. 22, 2018, https://clinicaltrials.gov/study/NCT03679598?tab=history&a=2#version-content-panel) (Year: 2018).*
Soy et al (Thorax. Aug. 23, 2006;61(12):1059-1064) (Year: 2006).*
Jonathan Robert Caronia, (Restrictive lung disease, Oct. 31, 2016) (Year: 2016).*
Polverino et al (Chest, vol. 152, Issue 2, Aug. 2017, pp. 249-262) (Year: 2017).*
Bhatti et al (Ann Thorac Med. Apr.-Jun. 2013; 8(2): 71-77) (Year: 2013).*
CCFA, (Treatment Options in IBD (inflammatory bowel disease), May 30, 2012) (Year: 2012).*
Peper et al. (Dose-Response, 7:172-192 (2009)) (Year: 2009).*

(Continued)

*Primary Examiner* — Jean P Cornet
(74) *Attorney, Agent, or Firm* — Wolff IP, a Prof. Corp.; Jessica R. Wolff

(57) ABSTRACT

The present invention discloses a dosage form and dosage regimen of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide (i.e. alvelestat) or salts thereof, and related methods of using the dosage form and dosage regimen.

20 Claims, 7 Drawing Sheets

(56) References Cited

FOREIGN PATENT DOCUMENTS

| | | | |
|---|---|---|---|
| WO | WO2007129060 A1 | 11/2007 | |
| WO | WO2007129962 A1 | 11/2007 | |
| WO | WO2007129963 A1 | 11/2007 | |
| WO | WO2007137080 A2 | 11/2007 | |
| WO | WO2007140117 A1 | 12/2007 | |
| WO | WO2008030158 A1 | 3/2008 | |
| WO | WO2008036379 A2 | 3/2008 | |
| WO | WO2008085608 A1 | 7/2008 | |
| WO | WO2008097676 A1 | 8/2008 | |
| WO | WO2008104752 A1 | 9/2008 | |
| WO | WO2009013444 A1 | 1/2009 | |
| WO | WO2009037413 A1 | 3/2009 | |
| WO | WO2009058076 A1 | 5/2009 | |
| WO | WO2009060158 A1 | 5/2009 | |
| WO | WO2009060206 A1 | 5/2009 | |
| WO | WO2009061271 A1 | 5/2009 | |
| WO | WO2010034996 A1 | 4/2010 | |
| WO | WO-2010094964 A1 * | 8/2010 | ............. A61P 43/00 |
| WO | WO2011039528 A1 | 4/2011 | |
| WO | WO2011103774 A1 | 9/2011 | |
| WO | WO2011110852 A1 | 9/2011 | |
| WO | WO2011110858 A1 | 9/2011 | |
| WO | WO2011110859 A1 | 9/2011 | |
| WO | WO2013037809 A1 | 3/2013 | |
| WO | WO2013084199 A1 | 6/2013 | |
| WO | WO2014009425 A1 | 1/2014 | |
| WO | WO2014029830 A1 | 2/2014 | |
| WO | WO2014029831 A1 | 2/2014 | |
| WO | WO2014029832 A1 | 2/2014 | |
| WO | WO2014122160 A1 | 8/2014 | |
| WO | WO2014135414 A1 | 9/2014 | |
| WO | WO2015091281 A1 | 6/2015 | |
| WO | WO2015096872 A1 | 7/2015 | |
| WO | WO2015096873 A1 | 7/2015 | |
| WO | WO2015124563 A1 | 8/2015 | |
| WO | 2015200349 A2 | 12/2015 | |
| WO | 2016/016364 A1 | 2/2016 | |
| WO | WO2016016363 A1 | 2/2016 | |
| WO | WO2016016365 A1 | 2/2016 | |
| WO | WO2016016366 A1 | 2/2016 | |
| WO | WO2016016368 A1 | 2/2016 | |
| WO | WO2016020070 A1 | 2/2016 | |
| WO | WO2016050835 A2 | 4/2016 | |
| WO | WO2017102674 A1 | 6/2017 | |
| WO | WO2017207430 A1 | 12/2017 | |
| WO | 2021053058 A1 | 3/2021 | |
| WO | 2021/178448 A1 | 9/2021 | |
| WO | 2021209739 A1 | 10/2021 | |

OTHER PUBLICATIONS

Stockley, R.A., et al., Alvelestat, an Oral Neutrophil Elastase Inhibitor in Alpha-1 Antitrypsin Deficiency (AATD): Results of a Phase II Trial; C15 Emerging COPD Diagnostics and Treatments / Mini Symposium / Walter E. Washington Convention Center, Ballroom B (Level 3), Am J Respir Crit Care Med, May 2023, 1 page, 207:A4493, www.atsjournals.org.

Alpha 1 Antitrypsin Deficiency (AATD), British Liver Trust, Registered Charity in England & Wales 298858, Scotland SC042140, Alpha-1-Factsheet_Apr-2019_v2.pdf (britishlivertrust.org.uk), 2 pages.

Barnes et al., "Targeting potential drivers of COVID-19: Neutrophil extracellular traps", J Exp Med. Jun. 1, 2020;217(6):e20200652. doi: 10.1084/jem.20200652.

Cao et al., "A Trial of Lopinavir—Ritonavir in Adults Hospitalized with Severe Covid-19", N Engl J Med. May 7, 2020;382(19):1787-1799. doi: 10.1056/NEJMoa2001282. Epub Mar. 18, 2020.

Carter et al., "The Fibrinogen Cleavage Product Aa-Val360 a Specific Marker of Neutrophil Elastase Activity in Vivo", Thorax. Aug. 2011;66(8):686-91. doi: 10.1136/thx.2010.154690. Epub May 26, 2011.

Chen et al., "Prevention of graft-versus-host disease while preserving graft versus-leukemia effect after selective depletion of host-reactive T cells by photodynamic cell purging process", Blood. May 1, 2002;99(9):3083-8. doi: 10.1182/blood.v99.9.3083.

Chen et al.,"Inability of memory T cells to induce graft-versus-host disease is a result of an abortive alloresponse", Blood. Apr. 1, 2007;109(7):3115-23. doi: 10.1182/blood-2006-04-016410.

Chen et al., "Transfer of allogeneic CD62L-memory T cells without graft-versus-host disease", Blood. Feb. 15, 2004;103(4):1534-41. doi: 10.1182/blood-2003-08-2987. Epub Oct. 9, 2003.

Cooke et al.,"Tumor necrosis factor-alpha production to lipopolysaccharide stimulation by donor cells predicts the severity of experimental acute graft-versus-host disease", J Clin Invest. Nov. 15, 1998;102(10):1882-91. doi: 10.1172/JCI4285.

Delbosc et al., "Elastase inhibitor AZD9668 treatment prevented progression of experimental abdominal aortic aneurysms", J Vasc Surg. Feb. 2016;63(2):486-92.e1. doi:10.1016/j.jvs.2014.07.102. Epub Aug. 28, 2014.

Elborn et al., "Efficacy safety and effect on biomarkers of AZD9668 in cystic fibrosis", Eur Respir J. Oct. 2012;40(4):969-76. doi: 10.1183/09031936.00194611. Epub Jan. 20, 2012.

Geleris et al., "Observational Study of Hydroxychloroquine in Hospitalized Patients with Covid-19", N Engl J Med. Jun. 18, 2020;382(25):2411-2418. doi: 10.1056/NEJMoa2012410. Epub May 7, 2020.

Grein et al., "Compassionate Use of Remdesivir for Patients with Severe Covid-19", N Engl J Med. Jun. 11, 2020;382(24):2327-2336. doi: 10.1056/NEJMoa2007016. Epub Apr. 10, 2020.

Groutas et al., "Neutrophil elastase inhibitors", Expert Opin Ther Pat. Mar. 2011;21(3):339-54. doi: 10.1517/13543776.2011.551115. Epub Jan. 16, 2011.

Hirsch et al., "Bronchiolitis obliterans syndrome after (heart-)lung transplantation. Impaired antiprotease defense and increased oxidant activity", Am J Respir Crit Care Med. Nov. 1999;160(5 Pt 1):1640-6. doi: 10.1164/ajrccm.160.5.9902012.

Horby et al., "Dexamethasone in Hospitalized Patients with Covid-19", N Engl J Med. Feb. 25, 2021;384(8):693-704. doi: 10.1056/NEJMoa2021436. Epub Jul. 17, 2020.

Ingraham et al., "Immunomodulation in COVID-19", Lancet Respir Med. Jun. 2020;8(6):544-546. doi: 10.1016/S2213-2600(20)30226-5. Epub May 4, 2020.

Kim et al., "Programmed Necrosis and Disease:We interrupt your regular programming to bring you necroinflammation", Cell Death Differ. Jan. 2019;26(1):25-40. doi: 10.1038/s41418-018-0179-3. Epub Oct. 22, 2018.

Lee et al., "Development and validation of a scale to measure symptoms of chronic graft-versus-host disease", Biol Blood Marrow Transplant. 2002;8(8):444-52. doi: 10.1053/bbmt.2002.v8.pm12234170.

Lee, Stephanie J, "Classification systems for chronic graft-versus-host disease", Blood. Jan. 5, 2017;129(1):30-37. doi: 10.1182/blood-2016-07-686642. Epub Nov. 7, 2016.

Li et al., "Neutrophil extracellular traps contribute to the pathogenesis of acid-aspiration-induced ALI/ARDS", Oncotarget. Nov. 28, 2017;9(2):1772-1784. doi: 10.18632/oncotarget.22744. eCollection Jan. 5, 2018.

Mcelvaney et al., "Characterization of the Inflammatory Response to Severe COVID-19 Illness", Am J Respir Crit Care Med. Sep. 15, 2020;202(6):812-821. doi: 10.1164/rccm.202005-1883OC.

Mercuro et al., "Risk of QT Interval Prolongation Associated With Use of Hydroxychloroquine With or Without Concomitant Azithromycin Among Hospitalized Patients Testing Positive for Coronavirus Disease 2019 (COVID-19)", JAMA Cardiol. Sep. 1, 2020;5(9):1036-1041. doi: 10.1001/jamacardio.2020.1834.

Meyer et al., "An international ISHLT/ATS/ERS clinical practice guideline: diagnosis and management of bronchiolitis obliterans syndrome", Eur Respir J. Dec. 2014;44(6):1479-503. doi: 10.1183/09031936.00107514. Epub Oct. 30, 2014.

Nath, et al., "Antihuman leukocyte antigen antibody-induced autoimmunity: role in chronic rejection", Curr Opin Organ Transplant. Feb. 2010;15(1):16-20. doi: 10.1097/MOT.0b013e3283342780.

Papayannopoulos et al., "Neutrophil elastase and myeloperoxidase regulate the formation of neutrophil extracellular traps", J Cell Biol. Nov. 1, 2010;191(3):677-91. doi: 10.1083/jcb.201006052. Epub Oct. 25, 2010.

(56) References Cited

OTHER PUBLICATIONS

Shlomchik, Warren D., "Graft-versus-host disease", Nat Rev Immunol. May 2007;7(5):340-52. doi: 10.1038/nri2000.
Sinden et al., "Proteinase 3 Activity in Sputum from Subjects with Alpha-1 Anti-trypsin Deficiency and COPD", Eur Respir J. May 2013;41(5):1042-50. doi: 10.1183/09031936.00089712. Epub Aug. 30, 2012.
Sinden et al., Alpha-1-Antitrypsin Variants and the Proteinase/Anti-Proteinase Imbalance in Chronic Obstructive Pulmonary Disease, Am J Physiol Lung Cell Mol Physiol. Jan. 15, 2015;308(2):L179-90. doi: 10.1152/ajplung.00179.2014.
Stevens et al., "AZD9668: pharmacological characterization of a novel oral inhibitor of neutrophil elastase", J Pharmacol Exp Ther. Oct. 2011;339(1):313-20. doi: 10.1124/jpet.111.182139. Epub Jul. 26, 2011.
Stockley, :Neutrophils and Protease/Antiprotease Imbalance, Am J Respir Crit Care Med. Nov. 1999;160(5 Pt 2): S49-52. doi: 10.1164/ajrccm.160.supplement_1.13.
Stone et al., "Elevated peptides in lung lavage fluid associated with bronchiolitis obliterans syndrome", PLoS One. Jan. 2, 2014;9(1):e84471. doi: 10.1371/journal.pone.0084471. eCollection 2014.
Thierry, Alain R., "Anti-protease Treatments Targeting Plasmin(ogen) and Neutrophil Elastase May Be Beneficial in Fighting COVID-19", Physiol Rev. Oct. 1, 2020;100(4):1597-1598. doi: 10.1152/physrev.00019.2020.
Verleden et al., "Chronic lung allograft dysfunction phenotypes and treatment", J Thorac Dis. Aug. 2017;9(8):2650-2659. doi: 10.21037/jtd.2017.07.81.
Verleden et al.,"Phenotypical Diversity of Airway Pathology in Chronic Pulmonary GvHD after Hematopoietic Stem Cell Transplantation", The Journal of Heart and Lung Transplantation, 38(4) S407-S408 (2019) DOI:https://doi.org/10.1016/j.healun.2019.01.1038.
Vultaggio et al., "Prompt predicting of early clinical deterioration of moderate-to-severe COVID-19 patients: usefulness of a combined score using IL-6 in a preliminary study", J Allergy Clin Immunol Pract. Sep. 2020;8(8):2575-2581.e2. doi: 10.1016/j.jaip.2020.06.013. Epub Jun. 19, 2020.
Wewers et al., "Replacement therapy for alpha 1-antitrypsin deficiency associated with emphysema", N Engl J Med. Apr. 23, 1987;316(17):1055-62. doi: 10.1056/NEJM198704233161704.
World Health Organization | COVID-19 Situation Report 142 Jun. 2020.
Zhang et al., "Allospecific CD4(+) effector memory T cells do not induce graft-versus-host disease in mice", Biol Blood Marrow Transplant. Oct. 2012; 18(10):1488-99. doi: 10.1016/j.bbmt.2012.07.009. Epub Jul. 15, 2012.
Zorzetto et al., "Serpina1 Gene Variants in Individuals from the General Population with Reduced α1-Antitrypsin Concentrations", Clin Chem. Aug. 2008;54(8):1331-8. doi: 10.1373/clinchem.2007.102798. Epub May 29, 2008.
Chua and Laurent, "Neutrophil elastase: mediator of extracellular matrix destruction and accumulation", Proc Am Thorac Soc. Jul. 2006;3(5):424-7. doi: 10.1513/pats.200603-078AW.
Anonymous: "Mereo BioPharma Announces Positive Desmosine Biomarker Data from an Interim analysis of an Investigator Initiated Study of alvelestat in Bronchiolitis Obliterans Syndrome (BOS)", Jun. 2, 2021 (Jun. 2, 2021), Retrieved from the internet: URL: https://www.mereobiopharma.com/news-and-events/news/2021/june/mereo-biopharma-announces-positive-desmosine-biomarker-data-from-an-interim-analysis-of-an-investigator-initiated-study-of-alvelestat-in-bronchiolitis-obliterana-syndrome-bos/.
Im et al., "63rd ASH Annual Meeting Abstracts, Poster Abstracts, 722.Allogeneic Transplantation: Acute and Chronic GVHD, Immune Reconstitution", Blood 138 (2021) 1815-1816.
International Search Report and Written Opinion issued Feb. 24, 2023 in PCT/EP2022/079286 (18 pages).
Narasaraju et al., "Neutrophilia and NETopathy as Key Pathologic Drivers of Progressive Lung Impairment in Patients With COVID-19", Front Pharmacol. Jun. 5, 2020;11:870. doi: 10.3389/fphar.2020.00870. eCollection 2020.
Mozzini and Girelli, "The role of Neutrophil Extracellular Traps in Covid-19: Only an hypothesis or a potential new field of research?", Thromb Res. Jul. 2020;191:26-27. doi: 10.1016/j.thromres.2020.04.031. Epub Apr. 27, 2020.
International Search Report issued Jun. 17, 2021 in PCT/GB2021/050653 (4 pages).
Written Opinion issued Jun. 17, 2021 in PCT/GB2021/050653 (10 pages).
International Preliminary Report on Patentability issued Oct. 13, 2022 in PCT/GB2021/050653 (11 pages).
International Search Report issued Dec. 9, 2020 in PCT/EP2020/075948 (4 pages).
Written Opinion issued Dec. 9, 2020 in PCT/EP2020/075948 (7 pages).
International Preliminary Report on Patentability issued Mar. 15, 2022 in PCT/EP2020/075948 (8 pages).
National Library of Medicine, "Alvelestat (MPH966), an Oral Neutrophil Elastase Inhibitor, in Bronchiolitis Obliterans Syndrome AfterAllogeneic Hematopoietic Stem Cell Transplantation", ClinicalTrials.gov ID NCT02669251, Version 1, Jan. 29, 2016, 19 pages.
National Library of Medicine, "Alvelestat (MPH966), an Oral Neutrophil Elastase Inhibitor, in Bronchiolitis Obliterans Syndrome AfterAllogeneic Hematopoietic Stem Cell Transplantation", ClinicalTrials.gov ID NCT02669251, Version 33, Jul. 30, 2019, 20 pages.
National Library of Medicine, "Alvelestat (MPH966), an Oral Neutrophil Elastase Inhibitor, in Bronchiolitis Obliterans Syndrome AfterAllogeneic Hematopoietic Stem Cell Transplantation", ClinicalTrials.gov ID NCT02669251, Version 40, Apr. 17, 2020, 20 pages.
National Library of Medicine, "Alvelestat (MPH966), an Oral Neutrophil Elastase Inhibitor, in Bronchiolitis Obliterans Syndrome AfterAllogeneic Hematopoietic Stem Cell Transplantation", ClinicalTrials.gov ID NCT02669251, Version 44, Feb. 16, 2021, 20 pages.
National Library of Medicine, "Alvelestat (MPH966), an Oral Neutrophil Elastase Inhibitor, in Bronchiolitis Obliterans Syndrome AfterAllogeneic Hematopoietic Stem Cell Transplantation", ClinicalTrials.gov ID NCT02669251, Version 53, Oct. 16, 2021, 20 pages.
National Library of Medicine, "Alvelestat (MPH966), an Oral Neutrophil Elastase Inhibitor, in Bronchiolitis Obliterans Syndrome AfterAllogeneic Hematopoietic Stem Cell Transplantation", ClinicalTrials.gov ID NCT02669251, Version 149, Oct. 8, 2022, 20 pages.
National Library of Medicine, "Alvelestat (MPH966), an Oral Neutrophil Elastase Inhibitor, in Bronchiolitis Obliterans Syndrome AfterAllogeneic Hematopoietic Stem Cell Transplantation", ClinicalTrials.gov ID NCT02669251, Version 245, Jun. 27, 2025, 21 pages.
National Library of Medicine, "A 12-week Study Treating Participants Who Have alpha1-antitrypsin-related COPD With Alvelestat (MPH966)or Placebo. (ASTRAEUS)", ClinicalTrials.gov ID NCT03636347, Version 1, Aug. 15, 2018, 9 pages.
National Library of Medicine, "A 12-week Study Treating Participants Who Have alpha1-antitrypsin-related COPD With Alvelestat (MPH966)or Placebo. (ASTRAEUS)", ClinicalTrials.gov ID NCT03636347, Version 10, Jun. 22, 2019, 11 pages.
National Library of Medicine, "A 12-week Study Treating Participants Who Have alpha1-antitrypsin-related COPD With Alvelestat (MPH966)or Placebo. (ASTRAEUS)", ClinicalTrials.gov ID NCT03636347, Version 14, May 1, 2020, 11 pages.
National Library of Medicine, "A 12-week Study Treating Participants Who Have alpha1-antitrypsin-related COPD With Alvelestat (MPH966)or Placebo. (ASTRAEUS)", ClinicalTrials.gov ID NCT03636347, Version 16, Jan. 7, 2021, 12 pages.
National Library of Medicine, "A 12-week Study Treating Participants Who Have alpha1-antitrypsin-related COPD With Alvelestat (MPH966)or Placebo. (ASTRAEUS)", ClinicalTrials.gov ID NCT03636347, Version 17, Aug. 10, 2021, 11 pages.
National Library of Medicine, "A 12-week Study Treating Participants Who Have alpha1-antitrypsin-related COPD With Alvelestat (MPH966)or Placebo. (ASTRAEUS)", ClinicalTrials.gov ID NCT03636347, Version 19, Apr. 6, 2022, 9 pages.

(56) References Cited

OTHER PUBLICATIONS

National Library of Medicine, "Alvelestat (MPH966) for the Treatment of ALpha-1 ANTitrypsin Deficiency (ATALANTa)", ClinicalTrials.gov ID NCT03679598, Version 1, Sep. 19, 2018, 10 pages.
National Library of Medicine, "Alvelestat (MPH966) for the Treatment of ALpha-1 ANTitrypsin Deficiency (ATALANTa)", ClinicalTrials.gov ID NCT03679598, Version 7, Jun. 12, 2019, 9 pages.
National Library of Medicine, "Alvelestat (MPH966) for the Treatment of ALpha-1 ANTitrypsin Deficiency (ATALANTa)", ClinicalTrials.gov ID NCT03679598, Version 10, Jun. 24, 2020, 11 pages.
National Library of Medicine, "Alvelestat (MPH966) for the Treatment of ALpha-1 ANTitrypsin Deficiency (ATALANTa)", ClinicalTrials.gov ID NCT03679598, Protocol Version 1.4, Feb. 16, 2021, 59 pages.
National Library of Medicine, "Alvelestat (MPH966) for the Treatment of ALpha-1 ANTitrypsin Deficiency (ATALANTa)", ClinicalTrials.gov ID NCT03679598, Version 13, Aug. 31, 2021, 11 pages.
National Library of Medicine, "Alvelestat (MPH966) for the Treatment of ALpha-1 ANTitrypsin Deficiency (ATALANTa)", ClinicalTrials.gov ID NCT03679598, Version 14, Aug. 23, 2022, 10 pages.
National Library of Medicine, "Alvelestat (MPH966) for the Treatment of ALpha-1 ANTitrypsin Deficiency (ATALANTa)", ClinicalTrials.gov ID NCT03679598, Version 24, Jul. 24, 2024, 17 pages.
National Library of Medicine, "COVID-19 Study of Safety and Tolerability of Alvelestat (COSTA)", ClinicalTrials.gov ID NCT04539795, Version 1, Sep. 3, 2020, 8 pages.
National Library of Medicine, "COVID-19 Study of Safety and Tolerability of Alvelestat (COSTA)", ClinicalTrials.gov ID NCT04539795, Version 2, Oct. 14, 2020, 8 pages.
National Library of Medicine, "COVID-19 Study of Safety and Tolerability of Alvelestat (COSTA)", ClinicalTrials.gov ID NCT04539795, Protocol Version 2.0, Apr. 20, 2021, 70 pages.
National Library of Medicine, "COVID-19 Study of Safety and Tolerability of Alvelestat (COSTA)", ClinicalTrials.gov ID NCT04539795, Version 4, Aug. 6, 2021, 7 pages.
National Library of Medicine, "COVID-19 Study of Safety and Tolerability of Alvelestat (COSTA)", ClinicalTrials.gov ID NCT04539795, Version 5, Nov. 16, 2021, 7 pages.
National Library of Medicine, "COVID-19 Study of Safety and Tolerability of Alvelestat (COSTA)", ClinicalTrials.gov ID NCT04539795, Version 8, Dec. 21, 2022, 14 pages.
International Preliminary Report on Patentability from PCT Application No. PCT/EP2022/079286 dated May 2, 2024, 10 pages.
Crocetii et al., "A patenting perspective on human neutrophil elastase {HNE) inhibitors (2014-2018) and their therapeutic applications", Expert Opin Ther Pal. Jul. 2019; 29{7):555-578. doi: 10.1080/13543776.2019.1630379. Epub Jun. 16, 2019.
De Brouwer et al., "Increased circulating desmosine and age-dependent elastinolysis in idiopathic pulmonary fibrosis",Respiratory Research, vol. 19, No. 1, Mar. 20, 2018, XP093024337.
Im et al., "Novel targets in the treatment of chronic graft-versus-host disease", Leukemia. Mar. 2017;31 (3):543-554. doi:10.1038/leu.2016.367. Epub Nov. 30, 2016.
Parkin et al., "Neutrophil Elastase Inhibitors for Use in the Treatment of Fibrosis", U.S. Appl. No. 18/692,523, filed Mar. 15, 2024.
Rodrigues et al., "Cutaneous Graft-Versus-Host Disease: Diagnosis and Treatment", Am J Clin Dermatol. Feb. 2018;19{1):33-50. doi: 10.1007/s40257-017-0306-9.
Stockley et al., "Phase II study of a neutrophil elastase inhibitor (AZD9668) in patients with bronchiectasis", Respir Med. Apr. 2013;107(4):524-33. doi: 10.1016/j.rmed.2012.12.009. Epub Feb. 20, 2013.
Zuo et al., "Neutrophil extracellular traps in COVID-19", JCI Insight. Jun. 4, 2020;5(11 ):e138999. doi: 10.1172/jci.insight.138999.
Anonymous: 11 Alvelestat (MPH966) for the Treatment of Alpha-1 ANTitrypsin Deficiency 11, Sep. 21, 2018 (Sep. 21, 2018), XP055810968, Retrieved from the Internet: URL:https://clinicaltrials.gov/ct2/show/NCT03679598 [retrieved on Sep. 22, 2022].
Von Nussbaum, Franz, "Neutrophil elastase inhibitors for the treatment of (cardio)pulmonary diseases: Into clinical testing with pre-adaptive pharmacophores", Bioorg Med Chem Lett. Oct. 15, 2015;25(20):4370-81. doi: 10.1016/j.omcl.2015.08.049. Epub Aug. 20, 2015.
International Search Report issued in PCT/GB2021/050653 on Jun. 17, 2021 (4 pages).
Written Opinion issued in PCT/GB2021/050653 on Jun. 17, 2021 (10 pages).
Prolastin-C Liquid, "Highlights of Prescribing Information", revised Sep. 2017, 22 pages.
Technical Annex, ATALANTa and ASTRAEUS, "Clinical Trial Results", submitted in EP App. No. 23187058.5 on Oct. 7, 2024, 3 pages.
International Search Report and Written Opinion from PCT Application No. PCT/GB2024/052624 dated Jan. 24, 2025, 17 pages.
International Search Report and Written Opinion from PCT Application No. PCT/GB2024/053186 dated Mar. 12, 2025, 17 pages.
International Search Report and Written Opinion from PCT Application No. PCT/GB2024/053187 dated Mar. 20, 2025, 12 pages.
Fettiplace et al., "Efficacy of Alvelestat on SGRQ in Patients with AATD and Mild Airflow Limitation: A Pooled Analysis from two Phase 2 Studies Methods", Aug. 13, 2024, Retrieved from the Internet, <https://www.mereobiopharma.com/media/g1npyszw/gold-pooled-analysis-poster_final_13august2024.pdf>, 1 page.
Kuna et al., "AZD9668, a neutrophil elastase inhibitor, plus ongoing budesonide/formoterol in patients with COPD", Respiratory Medicine, vol. 106, No. 4, Apr. 1, 2012, pp. 531-539.
Wells et al., "Alvelestat (MPH966) for the Treatment of ALpha-1 ANTitrypsin Deficiency (ATALANTa): A Phase 2, multicenter, double-blind, randomized, placebocontrolled study to evaluate efficacy, safety, and tolerability of alvelestat in alpha-1 antitrypsin deficiency", May 19, 2024, Retrieved from the Internet, <https://www.mereobiopharma.com/media/y a2hpbrh/ats2024_poster_atalanta_may2024.pdf>, 1 page.
Albarbarawi et al., "Characterization and validation of an isotope-dilution LC-MS/MS method for quantification of total desmosine and isodesmosine in plasma and serum", Bioanalysis, vol. 16, Aug. 2013, pp. 1991-2001.
Dransfield, "Alvelestat (MPH966) for the Treatment of Alpha-1 ANTitrypsin Deficiency (ATALANTa)", National Library of Medicine Dec. 15, 2023, 22 pages.
Huang et al., "Clinical validity of plasma and urinary desmosine as biomarkers for chronic obstructive pulmonary disease", Thorax, vol. 67, 2012. pp. 502-508.
Im et al., "Phase 1 Study of Alvelestat, an Oral Neutrophil Elastase Inhibitor, in Patients with Bronchiolitis Obliterans Syndrome after Hematopoietic Cell Transplantation", Blood, vol. 136, No. 1, 2020, pp. 18-19.
Mereo Biopharma Group, "Unlocking the potential of novel targets for cancer and rare diseases", Nov. 2020, 35 pages.
Nedergaard et al., "Type VI collagen turnover-related peptides—novel serological biomarkers of muscle mass and anabolic response to loading in young men", J Cachexia Sarcopenia Muscle, vol. 4, 2013, pp. 267-275.
Nielsen et al., "The neo-epitope specific Pro-C3 Elisa measures true formation of type III collagen associated with liver and muscle parameters", Am J Transl Res., vol. 5(3), 2013, pp. 303-315.
Organ et al., "Biomarkers of collagen synthesis predict progression in the Profile idiopathic pulmonary fibrosis cohort", Respiratory Research, vol. 20, 2019, pp. 148.
Quinn et al., "Obstacles to early diagnosis and treatment of alphal antitrypsin deficiency: current perspectives" Therapeutics and clinical risk management, 2020, pp. 1243-1255.
Ricard-Blum et al., "Molecular and tissue alterations of collagens in fibrosis", Matrix Biology vol. 68-69, Aug. 2018, pp. 122-149.
Schumann et al., "Collagen Degradation and Formation Are Elevated in Exacerbated COPD Compared With Stable Disease", Chest. vol. 154(4), Oct. 2018, pp. 798-807.
Tiberi et al., "Ertapenem in the treatment of multidrug-resistant tuberculosis: first clinical experience", Eur. Respir. J., vol. 47, 2016, pp. 333-336.

(56) References Cited

OTHER PUBLICATIONS

Verleden et al., “Chronic lung allograft dysfunction: Definition, diagnostic criteria, and approaches to treatment—A consensus report from the Pulmonary Council of the ISHLT”, The Journal of Heart and Lung Transplantation, vol. 38, No. 5, 2019, pp. 493-503.
Wozniak al., “Challenges and prospects for alpha-1 antitrypsin deficiency gene therapy” Human gene therapy, vol. 26, No. 11, 2015, pp. 709-718.
Communication of a notice of opposition from EP Application No. 21714345.2 dated May 28, 2024, 19 pages.
Elssner et al., “The role of neutrophils in the pathogenesis of obliterative bronchiolitis after lung transplantation”, Transplant Infectious Disease,2001, vol. 3, No. 3,pp. 168-176, <URL: https://doi.org/10.1034 j.1399-3062.2001.003003168.x>.
Meyer et al., “Neutrophils, Unopposed Neutrophil Elastase, and Alpha1-Antiprotease Defenses Following Human Lung Transplantation”, American Journal of Respiratory and Critical Care Medicine,2001, vol. 164, No. 1,pp. 97-102, <URL: https://doi.org/10.1164/ajrccm.164.1.2006096>.
Nunley et al., “Unopposed Neutrophil Elastase in Bronchoalveolar Lavage from Transplant Recipients with Cystic Fibrosis”, American Journal of Respiratory and Critical Care Medicine,1999, vol. 159, No. 1,pp. 258-261,<URL: https://doi.org/10.1164/ajrccm.159.1.9712068>.
International Search Report issued Jun. 17, 2021 in PCT/GB2021/050658 (4 pages).
Written Opinion ssued Jun. 17, 2021 in PCT/GB2021/050658 (10 pages).
International Preliminary Report on Patentability issued Oct. 13, 2022 in PCT/GB2021/0506580 (11 pages).
Gunawardena, et al., “Pharmacokinetics and safety of AZD9668, an oral neutrophil elastase inhibitor, in healthy volunteers and patients with COPD”, Int J Clin Pharmacol Ther, vol. 51, No. 4, 2013, pp. 288-304.
International Preliminary Report on Patentability issued in PCT/GB2021/050653 on Oct. 27, 2022 (12 pages).

* cited by examiner

METHODS INVOLVING NEUTROPHIL ELASTASE INHIBITOR ALVELESTAT FOR TREATING RESPIRATORY DISEASE MEDIATED BY ALPHA-1 ANTITRYPSIN DEFICIENCY

CROSS REFERENCE TO RELATED APPLICATIONS

The present invention is filed under 35 U.S.C. § 371 as the U.S. national phase of International Patent Application No. PCT/GB2021/050653, filed 16 Mar. 2021, which designated the United States, and which claims the benefit of priority to United Kingdom patent application number 2005519.0, filed 16 Apr. 2020; and United Kingdom patent application number 2005520.8, filed 16 Apr. 2020; and US provisional application U.S. 62/706,195, filed 4 Aug. 2020. The contents of these applications are incorporated herein by reference.

FIELD OF THE INVENTION

The present invention discloses a novel dosage form and dosage regimen of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide and salts thereof.

BACKGROUND OF THE INVENTION

Elastases are possibly the most destructive enzymes in the body, having the ability to degrade virtually all connective tissue components.

Human neutrophil elastase (hNE), a member of the chymotrypsin superfamily of serine proteases is a 33-KDa enzyme stored in the azurophilic granules of the neutrophils. In neutrophils the concentration of NE (neutrophil elastase) exceeds 5 mM and its total cellular amount has been estimated to be up to 3 pg. Upon activation, NE is rapidly released from the granules into the extracellular space (See Kawabat et al. 2002, Eur. J. Pharmacol. 451, 1-10). The main intracellular physiological function of NE is degradation of foreign organic molecules phagocytosed by neutrophils, whereas the main target for extracellular elastase is elastin (Janoff and Scherer, 1968, J. Exp. Med. 128, 1137-1155). NE is unique, as compared to other proteases (for example, proteinase 3) in that it has the ability to degrade almost all extracellular matrix and key plasma proteins (See Kawabat et al., 2002, Eur. J. Pharmacol. 451, 1-10), including elastin, Type 3 and type 4 collagens, laminin, fibronectin, cytokines, etc. (Ohbayashi, H., 2002, Expert Opin. Investig. Drugs, 11, 965-980). NE is a major common mediator of many pathological changes seen in chronic lung disease (Stockley, R. A. 1994, Am. J. Resp. Crit. Care Med. 150, 109-113).

The destructive role of NE was solidified almost 40 years ago when Laurell and Eriksson reported an association of chronic airflow obstruction and emphysema with deficiency of serum α1-antitrypsin (Laurel) and Eriksson, 1963, Scand. J. Clin. Invest. 15, 132-140), which was found to be the most important endogenous inhibitor of NE. The imbalance between NE and endogenous antiprotease is believed to cause excess NE in pulmonary tissues which is considered as a major pathogenic factor in chronic obstructive pulmonary disease (COPD). The excessive NE destroys normal pulmonary structures, followed by the irreversible enlargement of the respiratory airspaces, as seen mainly in emphysema. There is an increase in neutrophil recruitment into the lungs which is associated with increased lung elastase burden and emphysema in al-proteinase inhibitor-deficient mice (Cavarra et al., 1996, Lab. Invest. 75, 273-280). Individuals with higher levels of the NE-α1 protease inhibitor complex in bronchoalveolar lavage fluid show significantly accelerated decline in lung functions compared to those with lower levels (Betsuyaku et al. 2000, Respiration, 67, 261-267). Instillation of NE via the trachea in rats causes lung haemorrhage, neutrophil accumulation during acute phase and emphysematous changes during chronic phase (Karaki et al., 2002, Am. J. Resp. Crit. Care Med., 166, 496-500). Studies have shown that the acute phase of pulmonary emphysema and pulmonary haemorrhage caused by NE in hamsters can be inhibited by pre-treatment with inhibitors of NE (Fujie et al., 1999, Inflamm. Res. 48, 160-167).

Acute lung injury caused by endotoxin in experimental animals is associated with elevated levels of NE (Kawabata, et al., 1999, Am. J. Resp. Crit. Care, 161, 2013-2018). Acute lung inflammation caused by intratracheal injection of lipopolysaccharide in mice has been shown to elevate the NE activity in bronchoalveolar lavage fluid which is significantly inhibited by a NE inhibitor (Fujie et al., 1999, Eur. J. Pharmacol., 374, 117-125; Yasui, et al., 1995, Eur. Resp. J., 8, 1293-1299). NE also plays an important role in the neutrophil-induced increase of pulmonary microvascular permeability observed in a model of acute lung injury caused by tumour necrosis factor<x (TNFce) and phorbol myristate acetate (PMA) in isolated perfused rabbit lungs (Miyazaki et al., 1998, Am. J. Respir. Crit. Care Med., 157, 89-94).

NE has been implicated in the promotion or exacerbation of a number of diseases such as pulmonary emphysema, pulmonary fibrosis, adult respiratory distress syndrome (ARDS), ischemia reperfusion injury, rheumatoid arthritis and pulmonary hypertension.

The present invention discloses dosage forms and dosage regimens of 2-pyridione derivatives that are inhibitors of NE and homologous serine proteases such as proteinase 3 and pancreatic elastase, and are thereby useful in therapy.

WO 2005/026123, which is incorporated herein by reference in its entirety, teaches a class of NE inhibitors that are useful in therapy. WO 2005/026123 further discloses a specific NE inhibitor compound identified therein as 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide and salts thereof (Example 94, page 85). This compound is designated herein as compound (I). Compound (I) is also known as alvelestat, AZD9668, or MPH966.

(I)

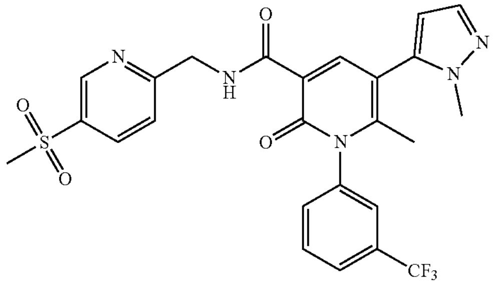

Similarly, WO 2010/094964, which is incorporated herein by reference in its entirety, teaches salt forms of compound (I), as shown above with respect to WO 2005/026123. This document reports that compound (I) is administered in a maximum daily amount of 200 mg per day.

Compound (I) may be useful in the treatment of diseases of the respiratory tract/system such as obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; adult respiratory distress syndrome (ARDS); lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, pulmonary hypertension, and infection due to respiratory syncytial virus, influenza, coronavirus (including SARS) and adenovirus.

There is a significant need for avoiding the initial activation of NE. Once activation has taken place, the inflammatory cascade that follows can cause irreversible damage, and itself is difficult to reverse. Therefore, the present invention aims to provide highly effective NE inhibition, by dose regimens of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide and salts thereof, that achieve and sustain blood levels at or above those needed to inhibit NE throughout the dosing period and in particular prevent the initial activation of NE.

SUMMARY OF THE INVENTION

In a first aspect, the present invention provides a solid dosage form comprising 120-300 mg of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof.

In an alternate first aspect, the present invention provides a solid dosage form comprising 220-300 mg of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof.

In a second aspect of the invention, the present invention provides a single or multiple solid dosage form(s) for oral administration of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof, for the treatment of a disease of the respiratory system which is mediated by α-1 antitrypsin deficiency, said single or multiple solid dosage form(s) comprising a total of 120-300 mg of 6-methyl-5-(l-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof per administration.

In an alternate second aspect of the invention, the present invention provides a single or multiple solid dosage form(s) for oral administration of 6-methyl-5-(l-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof, for the treatment of a disease of the respiratory system which is mediated by α-1 antitrypsin deficiency, said single or multiple solid dosage form(s) comprising a total of 220-300 mg of 6-methyl-5-(l-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof per administration.

In a third aspect of the invention, the present invention provides a single or multiple solid dosage form(s) for oral administration of 6-methyl-5-(l-methyl-1H-pyrazol-5-yl)-N-{([5-(methylsulfonyl)pyridin-2-yl]methyl}-2-oxo-1-[3-(trifluoromethyl)phenyl]-1,2-dihydropyridine-3-carboxamide or a salt thereof, for the treatment of a disease of the respiratory system which is mediated by α-1 antitrypsin deficiency, said single or multiple solid dosage form(s) comprising a total of 120-300 mg of 6-methyl-5-(l-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof per administration, and wherein the administration of each dose takes place twice daily, with at least 8 hours between administrations.

In an alternate third aspect of the invention, the present invention provides a single or multiple solid dosage form(s) for oral administration of 6-methyl-5-(l-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof, for the treatment of a disease of the respiratory system which is mediated by α-1 antitrypsin deficiency, said single or multiple solid dosage form(s) comprising a total of 220-300 mg of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof per administration, and wherein the administration of each dose takes place twice daily, with at least 8 hours between administrations.

In a fourth aspect of the invention, the present invention provides a kit comprising a plurality of solid dosage forms for oral administration of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof, said kit containing instructions for sequentially administering a total of 120-300 mg of said 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof per administration, and wherein the administration of each dose takes place twice daily, with at least 8 hours between administrations, for the treatment of a disease of the respiratory system which is mediated by α-1 antitrypsin deficiency.

In an alternate fourth aspect of the invention, the present invention provides a kit comprising a plurality of solid dosage forms for oral administration of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof, said kit containing instructions for sequentially administering a total of 220-300 mg of said 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof per administration, and wherein the administration of each dose takes place twice daily, with at least 8 hours between administrations, for the treatment of a disease of the respiratory system which is mediated by α-1 antitrypsin deficiency.

In a fifth aspect of the invention, the present invention provides a kit comprising a plurality of solid dosage forms for oral administration, each dosage form comprising 120-300 mg of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof, said kit containing instructions for sequential, twice daily administration of each dose, for the treatment of a disease of the respiratory system which is mediated by α-1 antitrypsin deficiency.

In an alternate fifth aspect of the invention, the present invention provides a kit comprising a plurality of solid dosage forms for oral administration, each dosage form comprising 220-300 mg of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof, said kit containing instructions for sequential, twice daily administration of each dose, for the treatment of a disease of the respiratory system which is mediated by α-1 antitrypsin deficiency.

In a sixth aspect of the invention, the present invention provides a method for treating a disease of the respiratory system which is mediated by α-1 antitrypsin deficiency, comprising the twice daily oral administration of a single or multiple solid dosage form(s), said single or multiple solid dosage form(s) comprising a total of 120-300 mg of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof per administration, to a human patient suffering from a disease of the respiratory system which is mediated by α-1 antitrypsin deficiency.

In an alternate sixth aspect of the invention, the present invention provides a method for treating a disease of the respiratory system which is mediated by α-1 antitrypsin deficiency, comprising the twice daily oral administration of a single or multiple solid dosage form(s), said single or multiple solid dosage form(s) comprising a total of 220-300 mg of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof per administration, to a human patient suffering from a disease of the respiratory system which is mediated by α-1 antitrypsin deficiency.

In a seventh aspect of the invention, the present invention provides a single or multiple solid dosage form(s) for oral administration of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof, for the treatment of COPD (Chronic Obstructive Pulmonary Disease), said single or multiple solid dosage form(s) comprising a total of 120-300 mg of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof per administration.

In an alternate seventh aspect of the invention, the present invention provides a single or multiple solid dosage form(s) for oral administration of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof, for the treatment of COPD (Chronic Obstructive Pulmonary Disease), said single or multiple solid dosage form(s) comprising a total of 220-300 mg of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof per administration.

In an eighth aspect of the invention, the present invention provides a single or multiple solid dosage form(s) for oral administration of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof, for the treatment of COPD (Chronic Obstructive Pulmonary Disease), said single or multiple solid dosage form(s) comprising a total of 120-300 mg of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof per administration, and wherein the administration of each dose takes place twice daily, with at least 8 hours between administrations.

In an alternate eighth aspect of the invention, the present invention provides a single or multiple solid dosage form(s) for oral administration of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof, for the treatment of COPD (Chronic Obstructive Pulmonary Disease), said single or multiple solid dosage form(s) comprising a total of 220-300 mg of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof per administration, and wherein the administration of each dose takes place twice daily, with at least 8 hours between administrations.

In a ninth aspect of the invention, the present invention provides a kit comprising a plurality of solid dosage forms for oral administration of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof, said kit containing instructions for sequentially administering a total of 120-300 mg of said 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof per administration, and wherein the administration of each dose takes place twice daily, with at least 8 hours between administrations, for the treatment of COPD (Chronic Obstructive Pulmonary Disease).

In an alternate ninth aspect of the invention, the present invention provides a kit comprising a plurality of solid dosage forms for oral administration of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof, said kit containing instructions for sequentially administering a total of 220-300 mg of said 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof per administration, and wherein the administration of each dose takes place twice daily, with at least 8 hours between administrations, for the treatment of COPD (Chronic Obstructive Pulmonary Disease).

In a tenth aspect of the invention, the present invention provides a kit comprising a plurality of solid dosage forms for oral administration, each dosage form comprising 120-300 mg of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof, said kit containing instructions for sequential, twice daily administration of each dose, for the treatment of COPD (Chronic Obstructive Pulmonary Disease).

In an alternate tenth aspect of the invention, the present invention provides a kit comprising a plurality of solid dosage forms for oral administration, each dosage form comprising 220-300 mg of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof, said kit containing instructions for sequential, twice daily administration of each dose, for the treatment of COPD (Chronic Obstructive Pulmonary Disease).

In an eleventh aspect of the invention, the present invention provides a method for treating COPD (Chronic Obstructive Pulmonary Disease), comprising the twice daily oral administration of a single or multiple solid dosage form(s), said single or multiple solid dosage form(s) comprising a total of 120-300 mg of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof per administration, to a human patient suffering from COPD.

In an alternate eleventh aspect of the invention, the present invention provides a method for treating COPD (Chronic Obstructive Pulmonary Disease), comprising the twice daily oral administration of a single or multiple solid dosage form(s), said single or multiple solid dosage form(s) comprising a total of 220-300 mg of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof per administration, to a human patient suffering from COPD.

Chronic Obstructive Pulmonary Disease (COPD) is an example of a disease of the respiratory system which is mediated by α-1 antitrypsin deficiency.

Regarding diseases of the respiratory system and NE, and in particular, COPD and NE, there is a clear pathological link as deficiency of α1-antitrypsin (AATD) is a specific risk factor for development of lung damage manifesting as COPD. The main physiological effect of al-antitrypsin is to neutralise NE. It is considered that it is the unopposed NE activity that drives lung tissue destruction in AATD related COPD, particularly emphysema. The lung is particularly susceptible for two reasons: (1) the day to day inhalation of noxious substances, in particular cigarette smoke, are powerful activators of neutrophils causing release of NE; (2) Elastin—the target of elastase is a major component of lung tissue (more so than other tissues) and without protection of NE inhibitors the elastin that supports delicate structures of the lung is broken down and the lung tissue progressively destroyed.

Hence, in all of the aspects of the invention, the disease of the respiratory system, in particular COPD is preferably associated with α1-antitrypsin deficiency (AATD). Similarly, in all of the aspects of the invention, the disease of the respiratory system, for example COPD is preferably treated via NE inhibition.

The present invention is not limited to a disease of the respiratory system associated with α1-antitrypsin deficiency (AATD). Indeed, other diseases, e.g. panniculitis, may be associated with α1-antitrypsin deficiency (AATD). Therefore, for each aspect of the invention described herein, there is also provided a further additional aspect where the disease can be any disease associated with α1-antitrypsin deficiency (AATD), for example panniculitis.

DETAILED DESCRIPTION OF THE INVENTION

Figure 1:
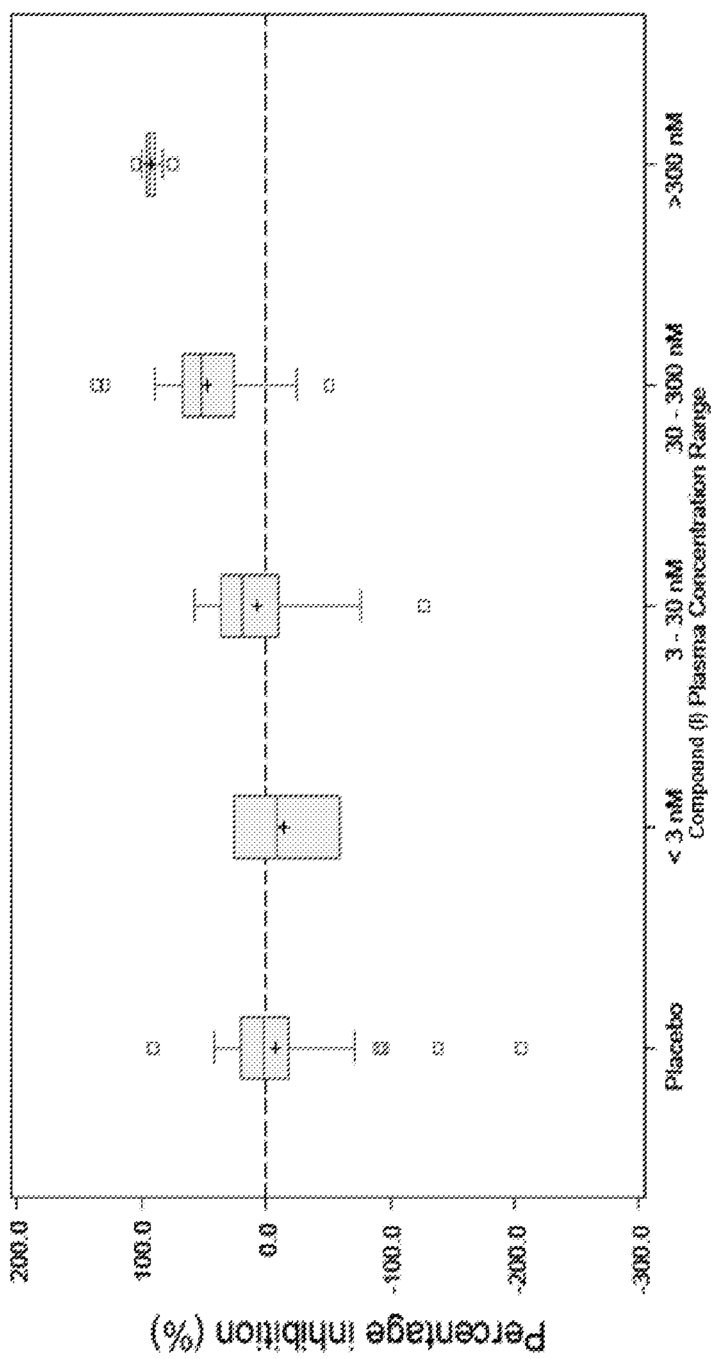
FIG. 1 shows a box plot of percentage inhibition of zymosan-stimulated NE activity in plasma by plasma PK concentration (Multiple Ascending Dose study). Note: the dot is the mean value. The line inside the box represents the median (50th percentile). The upper and lower edges of the box represent the 75th and 25th percentiles respectively, i.e. the inter quartile range (IQR). The whiskers represent the extent of the data with 1.5*IQR beyond the upper and lower percentiles. Outliers from this range are shown.

It has been determined that, to avoid NE activation, hence, avoid damage associated with NE in diseases of the respiratory system which are mediated by α-1 antitrypsin deficiency, such as COPD, inhibitory treatment must achieve and maintain a threshold Cmin (trough plasma concentration) in a human of 300 nM or above. This is shown in FIG. 1. Achieving and maintaining such a threshold Cmin is correlated with an increased chance of survival and better quality of life in such patients.

This requires a substantially higher dose of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide than was previously thought. For example, the prior art discloses that a maximum daily amount of 200 mg should be administered.

As used herein, a disease of the respiratory system which is mediated by α-1 antitrypsin deficiency includes asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; adult respiratory distress syndrome (ARDS); lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, pulmonary hypertension, and infection due to respiratory syncytial virus, influenza, coronavirus (including SARS) and adenovirus.

In a preferred embodiment, the disease of the respiratory system which is mediated by α-1 antitrypsin deficiency is chronic obstructive pulmonary disease (COPD). In another preferred embodiment, the disease of the respiratory system which is mediated by α-1 antitrypsin deficiency is emphysema. In another preferred embodiment, the disease of the respiratory system which is mediated by α-1 antitrypsin deficiency is bronchiectasis. In another preferred embodiment, the disease of the respiratory system which is mediated by α-1 antitrypsin deficiency is asthma.

As used herein, a disease of the respiratory system which is mediated by α-1 antitrypsin deficiency includes a patient with α-1 antitrypsin deficiency who is suffering from a disease of the respiratory system described herein, e.g. chronic obstructive pulmonary disease (COPD) or emphysema.

As used herein, a disease which is mediated by α-1 antitrypsin deficiency includes a patient with α-1 antitrypsin deficiency who is suffering from a disease. As used herein, a disease which is mediated by α-1 antitrypsin deficiency includes panniculitis.

Threshold $C_{min}$ values have been shown to be achieved and maintained when a patient suffering from a disease of the respiratory system which is mediated by α-1 antitrypsin deficiency is administered a 120 mg of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof, twice daily. Preferably, a minimum of 120 mg, twice per day is administered to the human patient suffering from a disease of the respiratory system which is mediated by α-1 antitrypsin deficiency, for example, COPD. Thus, a minimum total daily dose of 240 mg, preferably 440 mg, more preferably 480 mg is administered.

In further embodiments of the invention, a minimum of 180 mg of alvelestat or a salt thereof, twice per day is administered to the human patient suffering from a disease of the respiratory system which is mediated by α-1 antitrypsin deficiency, for example, COPD. Thus, a minimum total daily dose of 360 mg, preferably 540 mg, is administered.

Furthermore, such threshold $C_{min}$ values have been shown to be achieved and maintained when a patient suffering from a respiratory disease mediated by α-1 antitrypsin deficiency, for example COPD, is administered a 240 mg of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof, twice daily. Preferably, a minimum of 240 mg, twice per day is administered to the human patient suffering from a disease of the respiratory system which is mediated by α-1 antitrypsin deficiency, for example COPD. Thus, a minimum total daily dose of 440 mg, preferably 480 mg is administered.

$C_{min}$ is a term used in pharmacokinetics for the minimum blood plasma concentration reached by a drug prior to administration of a second dose. E.g. $C_{min}$ can be the trough plasma concentration observed in FIG. 2. $C_{min}$ is the opposite of $C_{max}$, the maximum concentration that the drug reaches (e.g. peak plasma concentration).

For all of the aspects of the invention disclosed herein, the administered alvelestat or a salt thereof results in a $C_{min}$ plasma concentration of at least 300 nM in the patient.

For all of the aspects of the invention disclosed herein, preferably the administered alvelestat or a salt thereof results in a $C_{max}$ plasma concentration of at least 1000 nM in the patient.

For all of the aspects of the invention disclosed herein, preferably the administered alvelestat or a salt thereof results in a $C_{min}$ plasma concentration of at least 300 nM and a $C_{max}$ plasma concentration of at least 1000 nM in the patient.

For all of the aspects of the invention disclosed herein, each dosage form is preferably a single solid entity. However, each administration may comprise a plurality of solid dosage forms, subject to each administration having no more than 300 mg of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof, and preferably 240-480 mg of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof.

Twice daily administration means that the administration takes place at regular spaced intervals, preferably at least 8 hours apart, more preferably at least 10 hours apart, for example about 12 hours apart±1 hour.

For all of the aspects of the invention disclosed herein, preferably a maximum daily dose of 600 mg is not exceeded, more preferably not more than 500 mg.

For all of the aspects of the invention disclosed herein, preferably each individual dose contains between 120 and 250 mg of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof, for example 120 mg, 180 mg or 240 mg.

For all of the aspects of the invention disclosed herein, preferably each individual dose contains between 160 and 250 mg of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof, e.g. 180 mg.

For all of the aspects of the invention disclosed herein, preferably each individual dose contains between 220 and 250 mg of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof, e.g. 240 mg.

The administration of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof preferably takes place chronically. Hence, a preferred embodiment of the fifth and tenth aspects of the invention, the kit comprises a defined supply of dosage forms, such as a weekly, bi-weekly or monthly supply of dosage forms of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof.

In an embodiment of the invention, the salt of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide is the tosylate salt of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide.

6-Methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide, or a salt thereof, may be administered to an individual in accordance with an effective dosing regimen for a desired period of time or duration, such as at least one week, at least about one month, at least about 2 months, at least about 3 months, at least about 6 months, at least about 12 months, at least about 24 months, or longer. For example, the compound may be administered on a daily or intermittent schedule for the duration of the subject's life.

The dose of 6-Methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof may be administered according to a dosage escalation regime in all methods of the invention. This allows safe titration up to a daily dose of alvelestat, e.g. of 120 mg twice daily (BID). For example, a dosage escalation regime up to a 120 mg twice daily dose of alvelestat according to the invention comprises administration of alvelestat or a salt thereof at a dose of 60 mg of alvelestat twice daily for a first period of time, followed by 120 mg twice daily thereafter. The first period may be from 5-20 days, preferably each about one week (7 days). In particular, alvelestat or a salt thereof is administered at 60 mg twice daily for one week, followed by 120 mg twice daily thereafter. Doses are referred to as the equivalent amount of alvelestat free base.

A dose escalation regime may also be used to allow safe titration up to a daily dose of alvelestat, e.g. of 240 mg twice daily (BID). For example, a dosage escalation regime up to a 240 mg twice daily dose of alvelestat according to the invention comprises administration of alvelestat or a salt thereof at a dose of 60 mg of alvelestat twice daily for a first period of time, followed by 120 mg twice daily for a second period of time, followed by 180 mg twice daily for a third period of time, and 240 mg twice daily thereafter. The first, second and third periods may each be from 5-20 days, preferably each about one week (7 days). In particular, alvelestat or a salt thereof is administered at 60 mg twice daily for one week, followed by 120 mg twice daily for one week, followed by 180 mg twice daily for one week, and 240 mg twice daily thereafter. Doses are referred to as the equivalent amount of alvelestat free base.

In an embodiment of the invention, the amount (e.g. mg) of alvelestat or a salt thereof referred to in the amount administered, the dose or the solid dosage form, is the corresponding amount of alvelestat free base in the alvelestat or salt thereof. For example, if a method of the invention requires the administration of a dose of 240 mg of alvelestat or a salt thereof, the amount of an alvelestat salt used will be equivalent to 240 mg of alvelestat freebase.

Figure 8:
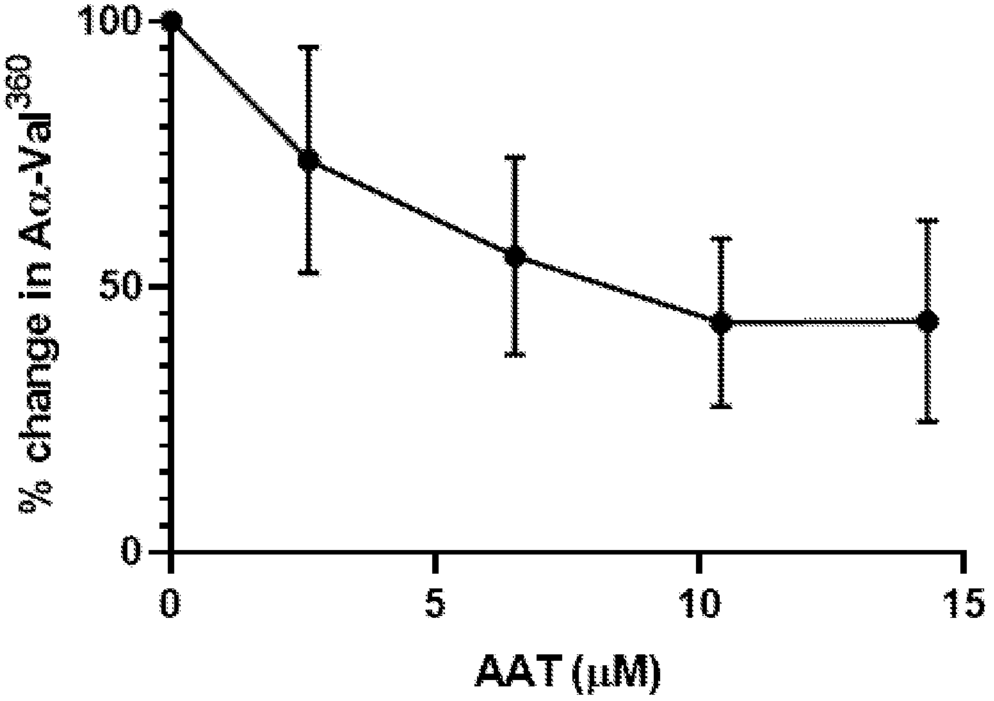
FIG. 8 shows that introduction of AAT into the imbalance model reduces NSP activity footprint, and the effect of increasing concentrations of active AAT on the activity neutrophil elastase activity within a model of proteinase/anti-proteinase imbalance. Percentage neutrophil elastase activity up to 15 μM with 0 μM AAT set as 100% activity baseline; n=4; mean+/− SEM.
Figure 9:
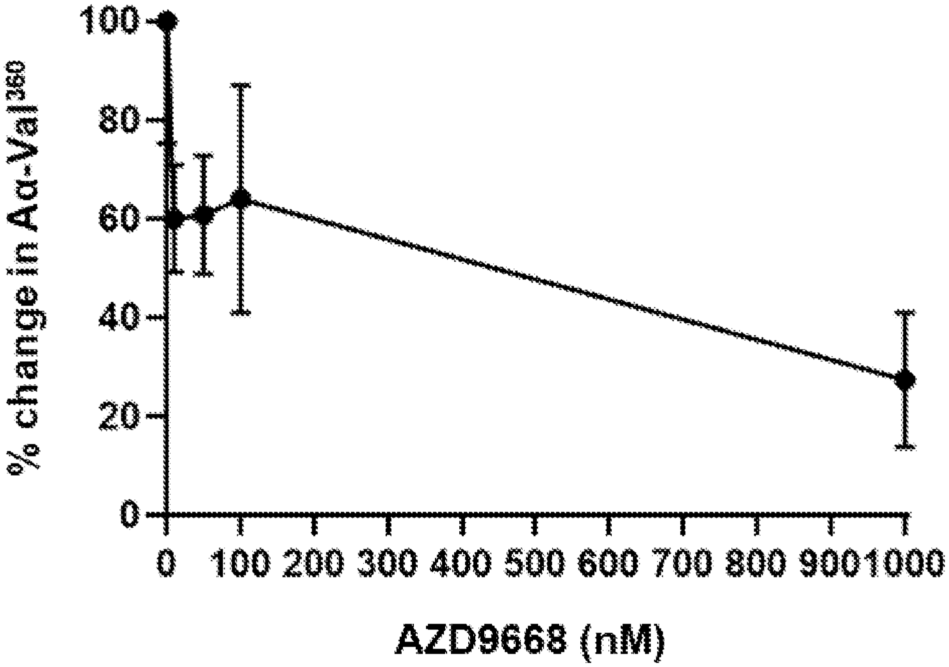
FIG. 9 shows the inhibitory effect of AZD9668 (alvelestat) on proteinase activity. Percentage change in activity produced by increasing concentrations of alvelestat (at 10 nM, 50 nM, 100 nM, 1000 nM) on the activity of neutrophil elastase within a model of proteinase/anti-proteinase imbalance. No inhibitor as 100% activity baseline. Error bars mean+/− SEM.

As shown in the examples, alvelestat $C_{max}$ concentrations achieved by the described dosing regimen suppressed neutrophil elastase (NE) activity by 72.6% (see FIG. 9). By contrast, AAT at concentrations achieved therapeutically in treatment of alpha-1 deficiency, by use of AAT replacement "augmentation", suppressed NE activity by only 56.7% (see FIG. 8). Thus, alvelestat may be a more potent inhibitor of NE than AAT augmentation therapy. It is therefore believed that alvelestat may be useful in treating patients who have not responded well to AAT augmentation therapy. Such augmentation therapy involves the administration of AAT intravenously in order to slow down progression of diseases of the respiratory system which are mediated by AATD.

Thus, the invention provides a method of treating a disease of the respiratory system which is mediated by α-1 antitrypsin deficiency (e.g. COPD) in a patient in need thereof who has not responded to AAT therapy, comprising administering an effective amount of alvelestat or a salt thereof as disclosed herein (e.g. 120-300 mg BID, in particular 220-300 mg BID) to the patient. In an embodiment, the administration of alvelestat or a salt thereof is either in place of, or in combination with, AAT augmentation therapy. Non-responders may be patients for whom AAT does not treat or delay progression of a disease of the respiratory system which is mediated by AATD, e.g. COPD.

Therefore, for all of the aspects of the invention disclosed herein, the patient in need of treatment may have previously been treated for α-1 antitrypsin deficiency, or is currently treated, by the administration of AAT. The compound (I) or salt thereof may be used alone when appropriate, or in the form of appropriate pharmaceutical composition comprising the compound of the invention in combination with a pharmaceutically acceptable diluent, adjuvant or carrier. Particularly preferred are compositions not containing material capable of causing an adverse reaction, for example, an allergic reaction.

The solid dosage form or forms as defined herein are preferably in the form of a tablet, tablets, capsule or capsules, most preferably a tablet.

According to the invention, there is provided a pharmaceutical composition comprising a compound (I) or salt thereof in admixture with a pharmaceutically acceptable diluent or carrier. The compound (I) or salt thereof is preferably used in a micronised or a milled form. The compound (I) or salt thereof is preferably less than 50% by weight and more preferably less than 30% by weight of the total composition weight in the compositions described herein (including the oral compositions).

For each and every method of this invention, the invention provides a further embodiment relating to a method of treatment comprising administering alvelestat or a salt thereof to a patient in need, in that method. For each and every method of this invention, the invention provides a further embodiment relating to alvelestat or a salt thereof for use in that method. For each and every method of this invention, the invention provides a further embodiment relating to alvelestat or a salt thereof in the manufacture of a medicament for that method.

In an embodiment of the methods described herein, alvelestat or a salt thereof is administered to a human patient in need thereof.

For oral administration the compound (I) or salts thereof may, for example, be admixed with an adjuvant, diluent or a filler, for example, lactose, saccharose, sorbitol, mannitol, dibasic calcium phosphate (dicalcium phosphate) including hydrated and anhydrous forms; a starch, for example, potato starch, corn (maize) starch or amylopectin; a cellulose derivative such as microcrystalline cellulose (MCC) or silicified microcrystalline cellulose (SMCC) and the like. In some embodiments mixtures of these may be used. In one embodiment the compound (I) tosylate is not admixed with mannitol. In one embodiment, the quantity of hydrophilic celluloses, such as MCC in the complete formulation ranges between 50% and 98%. These adjuvents, diluents and fillers are used in total in 60 to 98 parts, preferably in 70 to 95 parts, thereof per 100 parts of the solid formulation by weight. Examples of cellulose derivatives such as microcrystalline cellulose, include Avicel PHIOI, PH 102, PH 102 SCG, PH200, PH301, PH302, and PH-F20, Avicel RC-A591 NF. An example of silicified microcrystalline cellulose products is ProSolv 90 HD, a mixture of MCC and colloidal silicon dioxide (manufactured by JRS Pharma). Examples of dibasic calcium phosphate dihydrate products are Calipharm D (from ThermoPhos), ICL D (from ICL Performance Products), Calstar (FMC Biopolymer), Di-Cafos (Chemische Fabrik Budenheim), DI-TAB (Innophos) and Emcompress (JRS Pharma LP). Examples of dibasic calcium phosphate anhydrate are ICL A (from ICL Performance Products), Fuji Calin (from Fuji Chemicals), A-TAB (Innophos), Di-Cafos AN (Chemische Fabrik Budenheim) and Emcompress Anhydrous (JRS Pharma LP). Examples of mannitol products is Pearlitol DC 300 and Pearlitol SD200 (manufactured by Roquette). An example of a lactose product is Pharmatose DCL 15 (manufactured by DMV).

A binder may be optionally used, for example, hydroxypropyl cellulose (HPC), hydroxypropylmethyl cellulose (HPMC), polyvinylpyrrolidone (PVP) or gelatine and 0.5 to 10 parts, preferably 1 to 4 parts, thereof is used per 100 parts of the solid pharmaceutical formulation by weight. An example of hydroxypropyl cellulose includes HPC LF. Examples of hydroxypropylmethyl cellulose include PVP K30 and PVP K90.

Disintegrating agents include for example, carmellose calcium, carboxymethyl starch sodium, croscarmellose sodium, crospovidone (crosslinked polyvinylpyrrolidone) and the like, and 0.5 to 15 parts, preferably 2 to 10 parts, thereof is used per 100 parts of the solid pharmaceutical formulation by weight. Disintegrating agents are exemplified by Kollidon CL (manufactured by BASF).

Lubricants include magnesium stearate, calcium stearate, sucrose esters of fatty acids, sodium stearyl fumarate, stearic acid, polyethyleneglycol, wax, paraffin and the like. The amount of lubricant is between 0.05% and 5% and is preferably between 0.5% to 3.5%, wherein the % is by weight of the formulation.

Surfactants include sodium lauryl sulfate, polysorbate 80, hydrogenated oil, polyoxyethylene(160)polyoxypropylene (30)glycol, and the like. The amount of surfactant is less than 2%, suitably less than 1.5%, for example less than 1.1% wherein the % is by weight of the formulation.

EXAMPLES

Example 1

The effect of alvelestat on ex vivo zymosan-stimulated neutrophil elastase (NE) activity in whole blood was evaluated. Blood from healthy volunteers from a Multiple Ascending Dose (MAD) alvelestat study was collected at baseline (before alvelestat treatment) and on the different doses of alvelestat treatment or placebo. Citrated blood samples were incubated with zymosan, and the resulting NE activity was measured by a fluorogenic assay based on the generation of the fluorescent cleavage product, 7-amino-4-methylcoumarin. NE suppressive effect of alvelestat or placebo was expressed as the percentage inhibition of the pre-treatment (baseline) zymosan stimulated NE. Alvelestat concentrations were measured in plasma by protein precipitation followed by liquid chromatography and tandem mass spectrometry, measured at the same timepoints as NE activity. Plasma concentrations were grouped for analysis as <3 nM; 3-30 nm; 30-300 nM and >300 nM.

FIG. 1 shows the percentage inhibition of zymosan stimulated neutrophil elastase (NE) in plasma at increasing concentrations of alvelestat, and indicates that ~100% NE inhibition can be achieved by a plasma concentration of alvelestat of 300 nM or above.

Example 2

Figure 2:
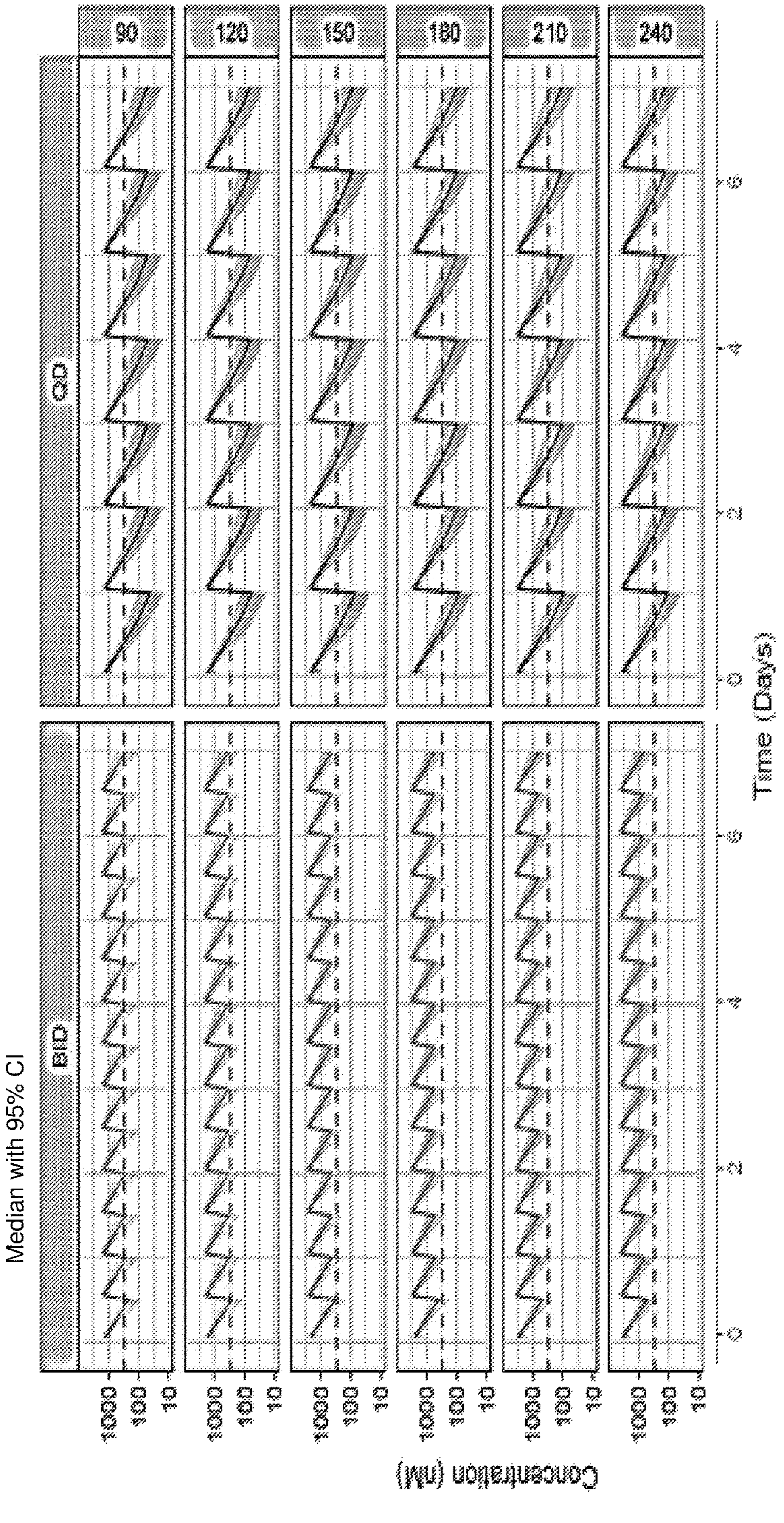
FIG. 2 shows population PK simulated median plasma concentration absolute values for the tosylate salt of doses of up to 240 mg given BID (twice daily) or QD (once daily) 6-methyl-5-(1-methyl-1H-pyrazol-5-yl)-N-{[5-(methylsulfonyl)pyridin yl]methyl}-2-oxo-1-[3-(trifluoromethyl)phenyl]-1,2-dihydropyridine-3-carboxamide, showing the 95% confidence intervals (CI) for trough concentrations ($C_{min}$).

FIG. 2 shows population PK simulated median plasma concentrations (dark line) for the tosylate salt of doses of up to 240 mg given BID (twice daily) or QD (once daily) 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide, showing the 95% Cl. The median and 95% CI bounds (in grey) show the predicted PK levels of 240 mg BID meet the greater than 300 nM threshold (dotted line). FIG. 2 also shows the predicted PK levels of 120 mg BID meet the 300 nM threshold (dotted line).

Table 1 shows population PK simulated median plasma concentrations for the tosylate salt of doses of up to 240 mg given BID (twice daily) or QD (once daily) 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide, showing the median, lower and upper interquartile ranges (IIQ and uIQ), lower and upper 95% CI (i95% CI) and u95% CI) for QD and BID dosing regimens. These all show that the predicted PK levels of 240 mg BID meet the greater than 300 nM threshold (dotted line). The median shows the predicted PK levels of 120 mg BID meet the greater than 300 nM threshold (dotted line).

It can be seen that in order to achieve a median threshold $C_{min}$ (trough plasma concentration) in a human of at least 300 nM, and allowing for up to 125% variance around the predicted $C_{min}$ as by Regulatory guidelines (EU and US regulators included), a minimum BID dose of 120 mg is required.

Preferably, in order to achieve a 95% CI lower threshold $C_{min}$ (trough plasma concentration) in a human of at least 300 nM, and allowing for up to 125% variance around the predicted $C_{min}$ as by Regulatory guidelines (EU and US regulators included), a minimum BID dose of 240 mg is preferred.

TABLE 1

PopPK Simulation plasma concentrations ($C_{min}$) for the tosylate salt

| | | Simulated PK concentration | | | | |
|---|---|---|---|---|---|---|
| Regimen | Dose (mg) | lIQ | Median | uIQ | l95% CI | u95% CI |
| QD | 90 | 31.842 | 50.145 | 72.7995 | 17.21465 | 120.5265 |
| QD | 120 | 41.5185 | 65.6745 | 98.8935 | 23.61045 | 156.442 |
| QD | 150 | 55.4215 | 85.3845 | 121.595 | 27.3528 | 205.093 |
| QD | 180 | 65.76775 | 94.012 | 145.8775 | 37.5023 | 230.9075 |
| QD | 210 | 73.145 | 106.665 | 161.475 | 39.1444 | 296.615 |
| QD | 240 | 83.544 | 131.075 | 187.1575 | 47.0317 | 317.0865 |
| BID | 90 | 196.1375 | 280.64 | 370.1475 | 107.781 | 530.043 |
| BID | 120 | 268.52 | 361.175 | 485.7125 | 155.359 | 727.246 |
| BID | 150 | 338.5225 | 449.28 | 584.6575 | 206.2275 | 825.7995 |
| BID | 180 | 390.1925 | 540.2 | 726.22 | 235.342 | 1012.285 |
| BID | 210 | 452.005 | 636.295 | 861.595 | 256.8515 | 1256.835 |
| BID | 240 | 504.2475 | 705.125 | 943.6825 | 288.7425 | 1369.025 |

Example 3 the protection of proteinase associated lung damage by alvelestat (a neutrophil elastase inhibitor)

Summary

Alpha-1 antitrypsin deficiency (AATD) is a genetic condition which can result in reduced/no release of the protective anti-proteinase alpha-1 antitrypsin (AAT). The lack of this major inhibitor of potentially destructive proteinases, results in a persistent proteinase/anti-proteinase imbalance state. Uninhibited proteinase, in particular elastase, activity causes structural changes to the lung and leads to emphysema and airway obstruction. Using an in vitro model of this imbalance allows for physiological assessment of the effect of elastase inhibitors on neutrophil serine proteinases (NSPs) involved in pathophysiology.

This example describes the effect of adding alvelestat into a stimulated neutrophil-fibrinogen buffer model to assess changes in elastase activity by monitoring the release of elastase specific markers of the process.

A model of the proteinase/anti-proteinase imbalance was developed and validated by describing the effect of the physiological inhibitor AAT on uninhibited NSP activity through elastase footprint activity immunoassays. Alvelestat was then added into the model.

Results obtained by adding alvelestat indicate that the compound is successfully and rapidly able to inhibit elastase activity in vitro and more effectively than the physiological inhibitor AAT.

Introduction

Alpha-1 antitrypsin deficiency (AATD) is a genetic condition arising from a mutation in the SERPINA1 gene [1] which encodes the glycoprotein alpha-1 antitrypsin (AAT) crucial for inhibition of destructive neutrophil serine proteinases. Mutation of the SERPINA1 gene produces AAT variants that lead to little/no secretion into the blood and tissues, thereby reducing physiological control of potentially damaging proteinases.

In healthy tissues, destructive proteinases are modulated by anti-proteinases (mostly AAT), however in AATD, the lack of AAT means these proteinases retain excessive activity; leading to a major proteinase/anti-proteinase imbalance [2] [3] [4].

This proteinase/anti-proteinase imbalance is believed to be the cause of the pathophysiological irreversible emphysematous changes associated with patients with AATD COPD (chronic obstructive pulmonary disease) [4].

Uninhibited proteinases are free to cleave major extracellular matrix (ECM) proteins, such as elastin, collagen and fibrinogen, damaging lung structure and leading to emphysema [5].

Indeed, clinically, an AAT serum concentration of below 11 μM is regarded as key to a non-physiological interaction resulting in increased emphysematous changes and hence clinical lung disease and is termed the putative "at-risk threshold" [6].

Historically, proteinase damage in COPD has been mostly attributed to neutrophil elastase (NE) activity, as demonstrated by animal studies [7].

Recent development of in vivo proteinase activity footprint immunoassays for NE, based upon detection of specific fibrinogen cleavage products in subject plasma, have supported the theory of the importance of the proteinase/anti-proteinase imbalance in AATD [8].

All deficient AAT phenotypes measured for NE activity demonstrated increased evidence of these footprints compared to healthy smoking volunteers, and demonstrated different profiles between AAT phenotypes [8].

It was hypothesised that the addition of alvelestat into the model would provide data on the effect of the drug in vitro, including exposure response to support dose ranging used in clinical trial, and support the products of this model as a biomarker of pharmaceutical and hence clinical efficacy.

The primary purpose of this model is to describe changes in elastase activity related to alvelestat NE inhibitor application.

Materials and Methods:

Enzyme Kinetics

The initial steps involved assessment of the biological activity of the enzymes and inhibitors to be used in the more physiological experiments.

Step 1 involved assessment of the activity of Porcine Pancreatic Elastase using Lineweaver-Burk reciprocal plot analysis [9].

Step 2 Having confirmed the PPE activity, the inhibitory function of a purified batch of AAT (Athens Research & Technology, US) was determined against this enzyme and used for all subsequent experiments.

Step 3 involved using the pure AAT to assess inhibition of pure NE preps (Athens Research and Technology, US) to derive their active function. The enzyme activity was then used to assess the activity of alvelestat.

Activity of alvelestat was calculated by measuring N-succinyl-Ala-Ala-Ala-p-nitroanilide (SlaaapN) cleavage when the compound was titrated against elastase of known concentration and activity [2]. Using these methods, alvelestat activity against NE was concluded to be 88%. Results were determined computationally using Prism software.

The Proteinase/Anti-Proteinase Imbalance Model

Neutrophils from healthy young volunteers were isolated using a method broadly described by Jepsen and Skottun [10].

Neutrophils were then incubated for 15 minutes at 37° C. with 550 nM fibrinogen (Calbiochem, San Diego, CA, US), 10 μM N-formyl-L-methionyl-L-leucyl-phenylalanine (fMLP; Sigma-Aldrich, St. Louis, MO, US), as well as concentrations of active AAT between 0-11 μM (Athens Research and Technology, Athens, GA, US) and increasing concentrations of AZD9668 in Roswell Park Memorial Institute media 1640

Figure 3:
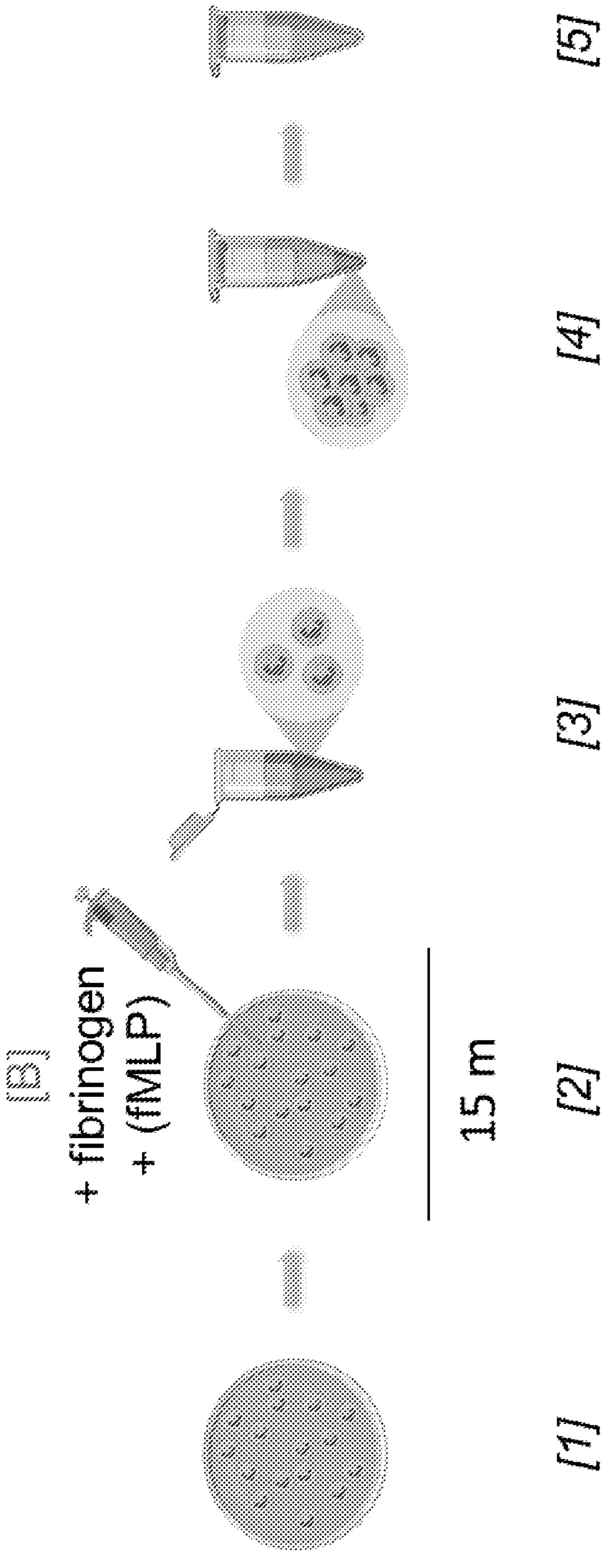
FIG. 3 shows a visualisation of proteinase/anti-proteinase imbalance model methodology. The following steps are shown. [1] plating of isolated neutrophils at 1 million cells/ml; [2] addition of substrate (fibrinogen) and stimulus (fMLP) beginning a 15 minute incubation period; [3] removal of treated cells from plate and centrifugation; [4-5] transfer of supernatant and disposal of cells. [B] indicates point of alvelestat addition to plated neutrophils alongside the addition of substrate and stimuli, namely "one-step" incubation.

(RPMI; Sigma-Aldrich; with L-glutamine and sodium bicarbonate) supplemented with Penicillin-streptomycin (1% v/v; Sigma-Aldrich)—FIG. 3.

Supernatant was obtained through centrifugation, and NE activity footprints were measured.

Specific Proteinase Activity Assays

Inverse fluorescence immunoassay methods described previously by Carter et aL and Newby et aL [8] were utilised to measured neutrophil elastase and proteinase 3 activity footprints.

Study Subjects

Healthy, young (<35 years old) non-smokers blood and plasma was collected with ethical approval under "Investigations of the ageing immune system" (ERN_12-1184) held by the Institute of Inflammation and Ageing, University of Birmingham.

Results

1. Development of a Novel In Vitro Model using Isolated Neutrophils in Fibrinogen Containing Buffer To generate an appropriate model for assessment of alvelestat, parameters involved in development of a fibrinogen-buffer neutrophil model were individually explored and optimal conditions selected.

i. Validation of the Aα-Val$^{360}$ Assay with Resting Neutrophils

Figure 4A:
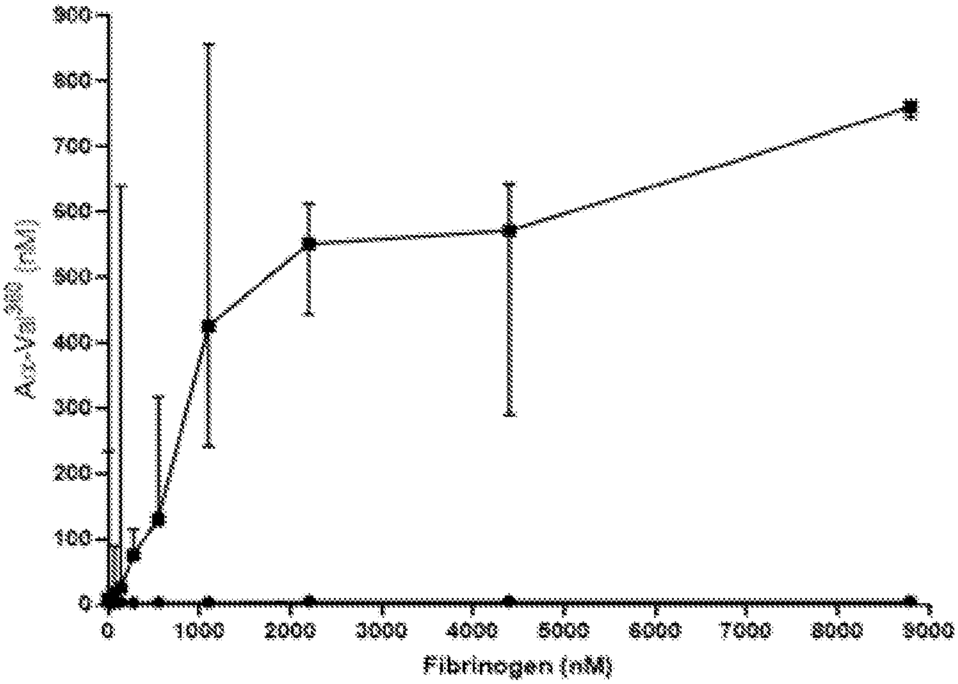
FIG. 4 shows that increasing fibrinogen within a closed model increases elastase signal. A Aα-$Val^{360}$ levels produced by 1 million neutrophils/ml when incubated with increasing concentrations of uncleaved fibrinogen over 60 minutes; ●=with neutrophils, ■=without neutrophils; n=3; error bars are median+/− IQR; B Quantity of Aα-$Val^{360}$ produced by 1 million neutrophils/ml when exposed to 550 nM uncleaved fibrinogen; n=3; normality determined by Shapiro-Wilk normality test; 0 to 550 significance determined by unpaired t-test; 550 to control significance determined by Mann-Whitney test; error bars mean+/− SEM.
Figure 4B:
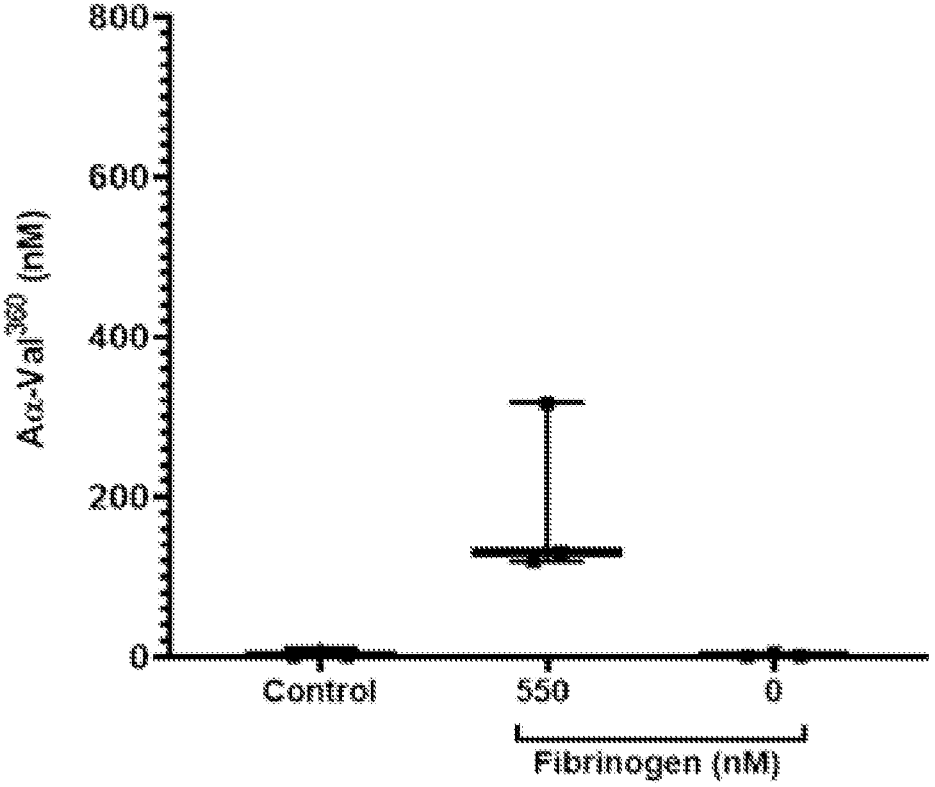

To select optimal fibrinogen concentrations, neutrophils were incubated along an uncleaved fibrinogen titration curve, ranging from 0-8797 nM. 8797 nM being the mean human blood fibrinogen concentration described in the literature. The curve was measured alongside a negative control with no neutrophils (see FIG. 4).

ii. Validation of the Aα-Va1360 Assay with Stimulated Neutrophils

To determine maximal stimulation a potent stimulator of neutrophils, Cal, [11] was titrated out from 0-2.4 μM and specific proteinase fibrinogen-cleavage product measured.

Figure 5:
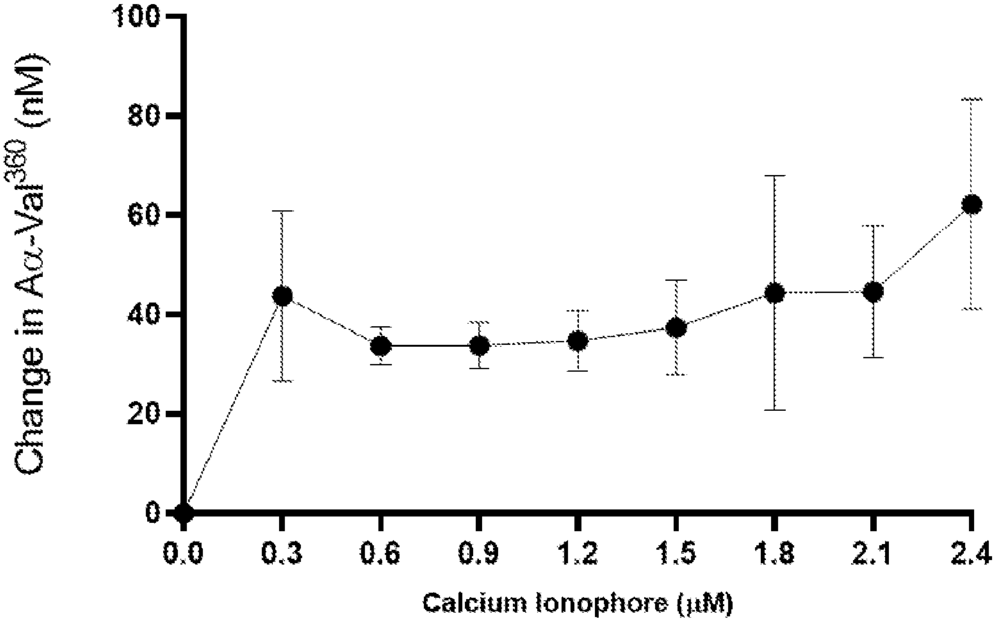
FIG. 5 shows proteinase activity following stimulation of neutrophils with Cal. Baseline corrected Aα-$Val^{360}$ levels following stimulation of neutrophils at 2.5 million/ml with Cal at 2.4/2.1/1.8/1.5/1.2/0.9/0.6/0.3 μM with fibrinogen (550 nM) for 60 minutes; n=3.

The NE activity footprint rose rapidly by 43.8 nM (+/−17.1) following stimulation of neutrophils with 0.3 μM Cal and then also plateaued (FIG. 5).

Flow cytometry confirmed neutrophil degranulation and, also, despite strong stimulation, neutrophil viability remained high. Flow cytometry assessment confirmed that DMSO used to dissolve alvelestat did not stimulate the neutrophils to degranulate.

To assess a more physiological stimulus, neutrophils were then incubated with N-formylmethionine-leucyl-phenylalanine (fMLP).

There was a rapid increase in proteinase activity observed with stimulations from 0-1 μM. At 0.1 μM.

Figure 6:
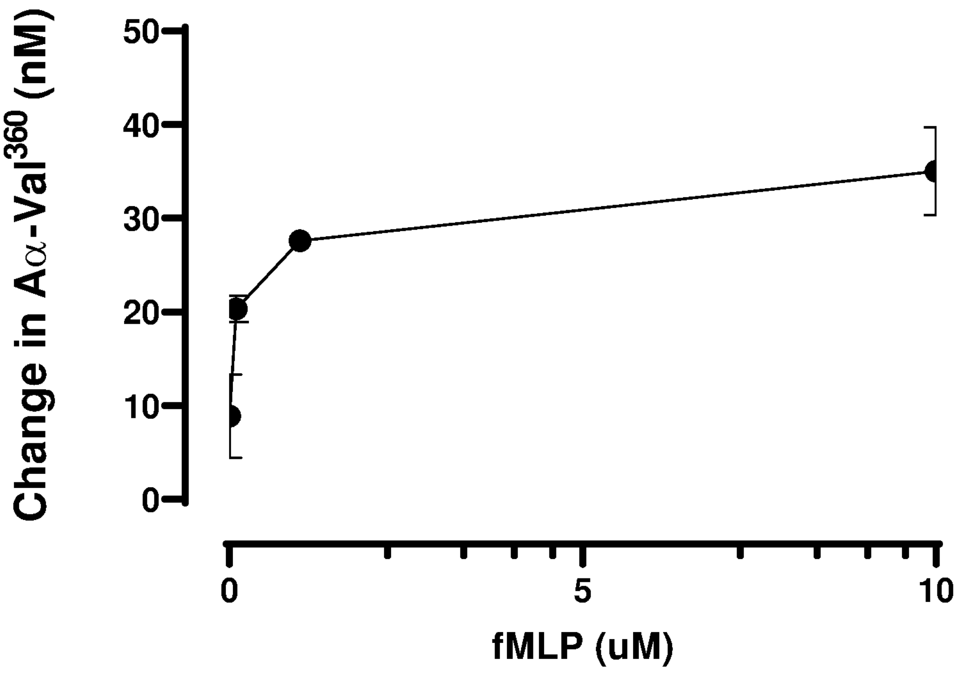
FIG. 6 shows proteinase activity following stimulation of neutrophils with fMLP. Change in Aα-$Val^{360}$ levels following stimulation of neutrophils at 2.5 million/ml with fMLP at 0, 0.1,1,10 μM fMLP with fibrinogen (550 nM) for 15 minutes; n=3.

At 0.1 μM, NE activity increased by 11.4 nM, and at 1 μM activity further increased by 7.3 nM. Activity continued to increase to 35.0 at 10 μM fMLP, although the rate of increase was less (FIG. 6).

Again, flow cytometry assessment confirmed that fMLP stimulated degranulation, with no affect cell viability and DMSO did not stimulate the neutrophils to degranulate.

2. Enzymatic Activity i. Porcine Pancreatic Elastase Activity

Prior to application of inhibitors, activity of PPE was determined by measuring substrate optical density over one hour, then the rate of reaction velocity and substrate cleavage were calculated. The Michaelis-Menten plot demonstrated a parabolic curve, so the reaction can be described by the usual Michaelis-Menten equation and is not cooperative or allosteric [12]. Change in absorbance (at 410 nm) of PPE incubated with 6 concentrations of substrate SlaaapN (N-succinyl-Ala-Ala-Ala-p-nitroanilide—CAS Number: 52299-14-6) over 15 minutes (450 seconds). A Lineweaver-Burk plot was also produced. Using the axis crosspoints obtained computationally, the values for maximal rate ($V_{max}$) and the Michaelis constant ($K_m$) could be calculated. N-Succinyl-Ala-Ala-Ala-p-nitroanilide can be a chromogenic substrate for chymotrypsin-like serine protease, pancreatic elastase and serine endopeptidase. Procedures for measuring elastase products using SlaaapN as the substrate are known.

Using these values and the known published value for catalytic efficiency [13], the functional activity of PPE could be determined and this value was used for subsequent experiments. PPE activity was concluded to be 81.5%.

ii. Alpha-1 Antitrypsin Activity

Activity of AAT was assessed kinetically by measuring SlaaapN cleavage by PPE of a known activity, following the incubation of a known active molar concentration of PPE with AAT.

Over time the amount of SlaaapN cleaved increased. As AAT:[active PPE] molar ratio increased, where higher concentrations of inhibitor were present, lower rates of cleavage occurred. With no AAT, PPE activity was 100%, and a molar concentration of 1.208 Mol AAT to 1 Mol PPE was required to neutralise PPE activity.

This meant 1.208 moles of AAT were required to inhibit 1 mol of active PPE. If AAT is fully active, PPE should be inhibited at 1:1. It can therefore be calculated that the functional AAT activity is therefore 83%.

iii. Neutrophil Elastase Activity

Activity of NE was then assessed kinetically by measuring SlaaapN cleavage by NE when inhibited with known active molar concentration AAT. Over time the amount of SlaaapN cleaved increased. As [active AAT]:NE molar ratio increased, where higher concentrations of inhibitor were present, lower rates of cleavage occurred.

This meant the pure active AAT inhibited NE at a molar ratio of 0.99:1 confirming the NE to be fully active.

iv. Alvelestat Activity

Activity of alvelestat was assessed kinetically by measuring substrate cleavage by elastase of known activity in the presence of the inhibitor, with inhibitor along an inhibition curve. Over time the amount of SlaaapN cleaved decreased.

Kinetic analysis demonstrated that alvelestat is a highly potent and rapid reversible inhibitor of NE [14]. The molar ratio of compound required to fully inhibit NE is 0.87:1, as outlined below.

We can conclude from this that by extrapolation 0.87 mole of alvelestat is required to inhibit 1 mole of NE. Therefore, activity within the errors of the experiment can be determined to be full.

TABLE 2

Figure 7:
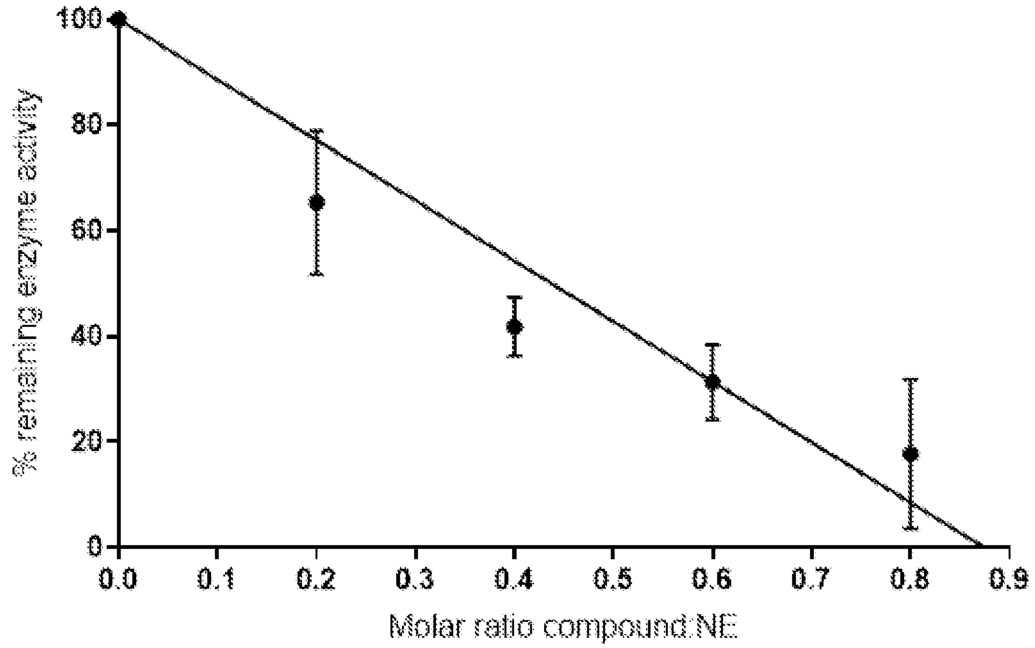
FIG. 7 shows assessment of alvelestat activity. Activity of alvelestat when in the presence of increasing concentrations of NE; n=4; error bars mean+/− SEM; line of best fit calculated using simple linear regression and with control fixed at 100%; normality determined using Shapiro-Wilk test.

| Computational intercept of axis in FIG. 7. Best-fit values | |
|---|---|
| Slope | −114.4 |
| X-intercept | 0.8742 |

Legend: Best-fit values of axis intercept and slope obtained by comparing alvelestat:NE ratios against calculated enzymatic activity of NE against SlaaapN in the presence of alvelestat.

3. The Generation of Serine Proteinase Peptides in the presence of Increasing Doses of AAT AAT was added in increasing functional concentrations to the proteinase/anti-proteinase model together with substrate (fibrinogen) and stimulus (fMLP). Pathophysiological concentrations were selected to mimic different disease genotype AAT concentrations as described by the American Thoracic and European Respiratory Societies: 0 μM representing a Pi 'null' genotype, 2.6-6.5 μM representing a PiZZ genotype, and 10.4-14.3 μM representing a PiSZ genotype [15].

As concentration of AAT increased, the proteinase activity signals reduced for NE and plateaued around 11 μM (FIG. 8). Examination of the change in activity by specific proteinase fibrinogen cleavage products (baseline set at 0 μM as 100% active) found that this represented a percentage decrease of 56.7% for NE (FIG. 8).

4. The Generation of Serine Proteinase Peptides in the presence of Increasing Doses of Alvelestat Alvelestat was added into the model along a dose response curve using pharmacologically active concentrations previously reported in the literature. When re-evaluated to take into account enzymatic activity, the effect of active alvelestat concentrations at 1000 nM, 100 nM, 50 nM, 10 nM and 0 nM on the activity of NE activity within a model of proteinase/anti-proteinase imbalance was assessed (n=3).

Data showed that when 10 nM of the compound was added into the model, change in activity defined by specific neutrophil elastase fibrinogen cleavage products (baseline set at 0 μM as 100% active) decreased to 60.1% for NE (FIG. 9). When treated with a higher concentration of 1000 nM, NE activity fell further to 27.4% of the untreated value.

Discussion

Literature describes alvelestat as a potent inhibitor of elastase in vitro [14] [16], and this is supported by data in this report using the proteinase/anti-proteinase biomarker model. It was observed that as the concentration of this anti-elastase increased, the quantity of specific elastase cleaved fibrinogen products rapidly decreased.

However, the inhibition of elastase activity occurred at a lower molar concentration than observed for AAT. This would imply that the compound could inhibit elastase which is not accessible to the larger AAT molecule indicating perhaps a cell membrane bound or intracellular inhibitory component.

There is limited published evidence describing the molecular interactions of alvelestat. We propose that the compound could therefore also be an effective inhibitor of cellular proteinase prior to substrate binding.

Summary Statements

This report demonstrates the effect of alvelestat on proteinase activity within a more physiological model of the proteinase/anti-proteinase imbalance relevant ton alpha-1 antitrypsin deficiency and its treatment.

The proteinase/anti-proteinase model data, collected in this example, supports a role for alvelestat as a potent inhibitor of elastase activity. Moreover the data supports that alvelestat can "normalise" the dysfunction associated with AATD associated disease, being more effective in suppressing elastase that the physiological AAT protein. The data also suggests the mode of action of the inhibitor exceeds that expected suggesting activity against NE is via a different mechanism to physiological inhibitors such as AAT. Alvelestat can, at concentrations achieved by the dosing regimens described in the application, provide NE inhibition greater than AAT at the protein concentration achieved by augmentation treatment in AATD. This supports the use of alvelestat as treatment of AATD, including in patients where augmentation has not worked, either as replacement to augmentation, or in combination with augmentation.

Further Summary Points:

1. Alvelestat or a salt thereof, at doses of 120-300 mg, and alternatively 220-300 mg, BID, demonstrates activity in inhibiting neutrophil elastase (NE). This can be seen from FIG. 1 where about 100% NE inhibition was observed at a plasma concentration of about 300 nM of alvelestat. Simulated PK modelling (FIG. 2) suggests that to achieve a plasma concentration of about 300 nM of alvelestat (or a salt thereof) in a subject, a dose of 120-300 mg BID is required. To have greater confidence in achieving a plasma concentration of about 300 nM of alvelestat (or a salt thereof), a dose of 220-300 mg BID is required. Lastly, example 3, shows that Alvelestat or a salt thereof, at doses of 120-300 mg, and alternatively 220-300 mg, BID, demonstrates activity in inhibiting neutrophil elastase (NE), e.g. as measured by A-α-$Val^{360}$ (FIG. 9). FIG. 9 shows that alvelestat at a concentration of 300 nm achieves NE inhibition via measuring percentage change in A-α-$Va1^{360}$. Example 3 also shows that A-α-$Val^{360}$ is a specific product of neutrophil elastase. A-α-$Val^{360}$ has been shown to be elevated in patients with AATD. A higher concentration of A-α-$Val^{360}$ is related to an increased severity of disease, e.g. AATD. Thus elevated levels of A-α-$Val^{360}$ in a patient may identify them as potential responders to treatment with alvelestat.

2. The NE inhibitory efficacy of alvelestat was compared to the NE inhibitory efficacy of AAT, the natural protein. Inhibition of NE by AAT plateaued at 56.7% inhibition (i.e. 43.3% above baseline—FIG. 8), whereas inhibition by alvelestat showed greater inhibition at 72.6% (i.e. 27.4% above baseline—FIG. 9) at 1000 nM of alvelestat. Here we show via simulated PK $C_{max}$ concentrations that concentrations of alvelestat at about 1000 nM would be achieved after dosing with the proposed doses/dosing regimens of the present invention (e.g. at doses of 120-300 mg, and 220-300 mg, BID) (Table 3). Table 3 shows selected population PK simulated Cmax plasma concentrations for alvelestat tosylate at doses of alvelestat of 120 mg and 240 mg given BID (twice daily), showing the median, lower and upper interquartile ranges (lIQ and uIQ), lower and upper 95% CI (l95% CI) and u95% CI) for BID dosing regimens. As can be seen, the values in Table 3 are 1000 nM or greater, and thus, the dosing regimens of the present invention provide the concentrations of alvelestat in order to achieve improved suppression of NE for therapeutic purposes compared to AAT at concentrations achieved therapeutically in treatment of alpha-1 deficiency, by use of AAT replacement "augmentation".

TABLE 3

PopPK Simulation plasma concentrations ($C_{max}$) for the tosylate salt

| | | Simulated PK concentration (nM) | | | | |
|---|---|---|---|---|---|---|
| Regimen | Dose (mg) | lIQ | Median | uIQ | l95% CI | u95% CI |
| BID | 120 | 1323.7 | 1485.25 | 1668.35 | 999.4453 | 2014.123 |
| BID | 240 | 2648.4 | 2953.5 | 3247.175 | 1991.09 | 3937.693 |

3. Alvelestat surprisingly showed higher potency in comparison to the natural inhibitor (AAT). This effect could be due to the ability of alvelestat to inhibit cell surface elastase (which AAT inhibits poorly due to steric hindrance). The effect could also be due to the ability of alvelestat to inhibit exosome containing elastase, which is released on neutrophil activation (but is resistant to AAT), because AAT cannot enter cells so cannot result in intracellular inhibition.

REFERENCES

1. Zorzetto, M., et al., SERPINA1 Gene Variants in Individuals from the General Population with Reduced α1-Antitrypsin Concentrations. Clinical Chemistry, 2008. 54(8): p. 1331.
2. Sinden, N. J. and R. A. Stockley, Proteinase 3 Activity in Sputum from Subjects with Alpha-1 Anti-trypsin Deficiency and COPD. European Respiratory Journal, 2013. 41: p. 1042-1050.
3. Sinden, N. J., et al., Alpha-1-Antitrypsin Variants and the Proteinase/Anti-Proteinase Imbalance in Chronic Obstructive Pulmonary Disease. American Journal of Physiology, Lung Cellular and Molecular Physiology, 2015. 308: p. 12.
4. Stockley, R. A., Neutrophils and Protease/Antiprotease Imbalance. American Journal of Respiratory and Critical Care Medicine, 1999. 160: p. S49-S52.
5. Rao, N. V., et al., Characterisation of Proteinase 3 (PR-3), a Neutrophil Serine Proteinase: Structural and Functional Properties. The Journal of Biological Chemistry, 1991. 266(15): p. 9540-9548.
6. Wewers, M. D., et al., Replacement therapy for alpha 1-antitrypsin deficiency associated with emphysema. N Engl J Med, 1987. 316(17): p. 1055-62.
7. Lucey, E. C., et al., Effect of Combined Human Neutrophil Cathepsin G and Elastase on Induction of Secretory Cell Metaplasia and Emphysema in Hamsters, with in vitro Observations on Elastolysis by these Enzymes. American Review of Respiratory Disease, 1985. 132(2): p. 362-366.
8. Carter, R. I., et al., The Fibrinogen Cleavage Product Aα-Val360, a Specific Marker of Neutrophil Elastase Activity in Vivo. Thorax, 2015. 66: p. 7.
9. Lineweaver, H. and D. Burk, The Determination of Enzyme Dissociation Constants, in The Fertilizer Investigations Unit, Bureau of Chemistry and Soils, United States, Department of Agriculture. 1934. p. 658-66.
10. Jepsen, L. V. and T. Skottun, A Rapid One-step Method for the Isolation of Human Granulocytes from Whole Blood. Scandinavian Journal of Clinical and Laboratory Investigation, 1982. 42(3): p. 235-238.
11. Lefrancais, E., et al., IL-33 is Processed Into Mature Biosactive Forms by Neutrophil Elastase and Cathepsin G. Proceedings of the National Academy of Sciences of the United States of America, 2012. 109(5): p. 6.
12. Michaelis, L. and M. L. Menten, Die Kinetik der Invertinwirkung. Biochemische Zeitschrift, 1913. 26: p. 333-69.
13. Nakajima, K., et al., Mapping the Extended Substrate Binding Site of Cathepsin G and Human Leukocyte Elastase. Studies with Peptide Substrates Related to the Alpha 1-protease Inhibitor Reactive Site. J Biol Chem, 1979. 254(10): p. 4027-32.
14. Stevens, T., et al., AZD9668: Pharmacological Characterization of a Novel Oral Inhibitor of Neutrophil Elastase. Journal of Pharmacology and Experimental Therapeutics, 2011. 339(1): p. 313.
15. American Thoracic Society/European Respiratory Society, American Thoracic Society/European Respiratory Society Statement. American Journal of Respiratory and Critical Care Medicine, 2003. 168(7): p. 818-900.
16. Gunawardena, K. A., H. Gullstrand, and J. Perrett, Pharmacokinetics and safety of AZD9668, an oral neutrophil elastase inhibitor, in healthy volunteers and patients with COPD. Int J Clin Pharmacol Ther, 2013. 51(4): p. 288-304.

The invention also provides the following numbered embodiments:

1. A solid dosage form comprising 120-300 mg of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide and salts thereof.
2. A single or multiple solid dosage form(s) for oral administration of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof, for the treatment of a disease of the respiratory system which is mediated by α-1 antitrypsin deficiency, said single or multiple solid dosage form(s) comprising a total of 120-300 mg of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof per administration.
3. A single or multiple solid dosage form(s) for oral administration of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof, for the treatment of a disease of the respiratory system which is mediated by α-1 antitrypsin deficiency, said single or multiple solid dosage form(s) comprising a total of 120-300 mg of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof per administration, and wherein the administration of each dose takes place twice daily, with at least 8 hours between administrations.
4. A kit comprising a plurality of solid dosage forms for oral administration of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof, said kit containing instructions for sequentially administering a total of 120-300 mg of said 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof per administration, wherein the administration of each dose takes place twice daily, with at least 8 hours between administrations, for the treatment of a disease of the respiratory system which is mediated by α-1 antitrypsin deficiency.
5. A kit comprising a plurality of solid dosage forms for oral administration, said dosage forms comprising 120-300 mg of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof, said kit containing instructions for sequential, twice daily administration of each dose, for the treatment of a disease of the respiratory system which is mediated by α-1 antitrypsin deficiency.
6. A method for treating a disease of the respiratory system which is mediated by α-1 antitrypsin deficiency, comprising the twice daily oral administration of a single or multiple solid dosage form(s), said single or multiple solid dosage form(s) comprising a total of 120-300 mg of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof per administration, to a human patient suffering from COPD.

7. The dosage form, kit or method according to any preceding embodiment, wherein the active ingredient comprises or consists of the tosylate salt of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide.
8. The dosage form, kit or method according to any preceding embodiment, wherein the 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide is present in the dosage form or forms in an amount of 120-300 mg, preferably 240-280 mg, most preferably 240 mg.
9. The solid dosage form as defined in any preceding embodiment, in the form of a tablet, tablets, capsule or capsules, preferably a tablet.
10. The dosage form kit or method according to any preceding embodiment, wherein the minimum total daily dose is 240 mg, preferably 480 mg.
11. The dosage form kit or method according to any preceding embodiment, wherein the disease of the respiratory system which is mediated by α-1 antitrypsin deficiency is selected from the group consisting of asthma, chronic obstructive pulmonary disease (COPD); bronchitis, emphysema; bronchiectasis; cystic fibrosis; sarcoidosis; farmer's lung, hypersensitivity pneumonitis, adult respiratory distress syndrome (ARDS), lung fibrosis, tuberculosis, aspergillosis, antitussive activity, iatrogenic cough, acute and chronic rhinitis, acute viral infection, pulmonary hypertension, infection due to respiratory syncytial virus, influenza, coronavirus and adenovirus.
12. The dosage form kit or method according to any preceding embodiment, wherein the disease of the respiratory system which is mediated by α-1 antitrypsin deficiency is COPD (Chronic Obstructive Pulmonary Disease).

1. A solid dosage form comprising 220-300 mg of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide and salts thereof.
2. A single or multiple solid dosage form(s) for oral administration of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof, for the treatment of a disease of the respiratory system which is mediated by α-1 antitrypsin deficiency, said single or multiple solid dosage form(s) comprising a total of 220-300 mg of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof per administration.
3. A single or multiple solid dosage form(s) for oral administration of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof, for the treatment of a disease of the respiratory system which is mediated by α-1 antitrypsin deficiency, said single or multiple solid dosage form(s) comprising a total of 220-300 mg of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof per administration, and wherein the administration of each dose takes place twice daily, with at least 8 hours between administrations.
4. A kit comprising a plurality of solid dosage forms for oral administration of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof, said kit containing instructions for sequentially administering a total of 220-300 mg of said 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof per administration, wherein the administration of each dose takes place twice daily, with at least 8 hours between administrations, for the treatment of a disease of the respiratory system which is mediated by α-1 antitrypsin deficiency.
5. A kit comprising a plurality of solid dosage forms for oral administration, said dosage forms comprising 220-300 mg of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof, said kit containing instructions for sequential, twice daily administration of each dose, for the treatment of a disease of the respiratory system which is mediated by α-1 antitrypsin deficiency.
6. A method for treating a disease of the respiratory system which is mediated by α-1 antitrypsin deficiency, comprising the twice daily oral administration of a single or multiple solid dosage form(s), said single or multiple solid dosage form(s) comprising a total of 220-300 mg of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof per administration, to a human patient suffering from COPD.
7. The dosage form, kit or method according to any preceding embodiment, wherein the active ingredient comprises or consists of the tosylate salt of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide.
8. The dosage form, kit or method according to any preceding embodiment, wherein the 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide is present in the dosage form or forms in an amount of 240-300 mg, preferably 240-280 mg, most preferably 240 mg.
9. The solid dosage form as defined in any preceding embodiment, in the form of a tablet, tablets, capsule or capsules, preferably a tablet.
10. The dosage form kit or method according to any preceding embodiment, wherein the minimum total daily dose is 440 mg, preferably 480 mg.
11. The dosage form kit or method according to any preceding embodiment, wherein the disease of the respiratory system which is mediated by α-1 antitrypsin deficiency is selected from the group consisting of asthma, chronic obstructive pulmonary disease (COPD); bronchitis, emphysema; bronchiectasis; cystic fibrosis; sarcoidosis; farmer's lung, hypersensitivity pneumonitis, adult respiratory distress syndrome (ARDS), lung fibrosis, tuberculosis, aspergillosis, antitussive activity, iatrogenic cough, acute and chronic rhinitis, acute viral infection, pulmonary hypertension, infection due to respiratory syncytial virus, influenza, coronavirus and adenovirus.

12. The dosage form kit or method according to any preceding embodiment, wherein the disease of the respiratory system which is mediated by α-1 antitrypsin deficiency is COPD (Chronic Obstructive Pulmonary Disease).

The invention claimed is:

1. A method for treating a disease of the respiratory system which is mediated by α-1 antitrypsin deficiency, comprising a twice daily oral administration of 220-250 mg of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof per administration to a subject in need thereof, wherein said disease is COPD (Chronic Obstructive Pulmonary Disease).

2. The method of claim 1, wherein he compound administered comprises the tosylate salt of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide.

3. The method of claim 1, wherein the minimum total daily dose is 480 mg.

4. The method of claim 1, wherein said COPD is chronic bronchitis.

5. The method of claim 1, wherein said COPD is emphysema.

6. The method of claim 1, wherein the minimum total daily dose is 440 mg.

7. The method of claim 1, wherein the administered 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof results in a $C_{min}$ plasma concentration of at least 300 nM in said patient.

8. The method of claim 1, wherein the administered 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof results in a $C_{max}$ plasma concentration of at least 1000 nM in said patient.

9. The method of claim 1, wherein the administered 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide or a salt thereof results in a $C_{min}$ plasma concentration of at least 300 nM and a $C_{max}$ plasma concentration of at least 1000 nM in said patient.

10. The method of claim 1, wherein 240 mg of 6-methyl-5-(1-methyl-1H-pyrazol-5-yl)-N-{[5-(methylsulfonyl)pyridin-2-yl]methyl}-2-oxo-1-[3-(trifluoromethyl)phenyl]1,2-dihydropyridine-3-carboxamide or a salt thereof is administered per administration.

11. The method of claim 1 wherein each administration of the said twice daily oral administration is an administration of a single solid dosage form.

12. The method of claim 1, wherein each administration of the said twice daily oral administration is an administration of multiple solid dosage forms.

13. A method of treating a disease of the respiratory system which is mediated by α-1 antitrypsin deficiency, comprising administering 220-250 mg BID of alvelestat or a salt thereof to a patient in need thereof, wherein said patient has not responded to a previous α-1 antitrypsin (AAT) therapy, and wherein said disease is COPD (Chronic Obstructive Pulmonary Disease).

14. The method of claim 13, wherein said COPD is emphysema.

15. The method of claim 13, wherein said COPD is chronic bronchitis.

16. The method of claim 13, wherein 240 mg BID of alvelestat or a salt thereof is administered to said patient.

17. A method of treating a disease of the respiratory system which is mediated by α-1 antitrypsin deficiency in a patient in need thereof, comprising administering alvelestat or a salt thereof comprising:

administering alvelestat or a salt thereof at a dose of 60 mg twice daily for a first period of time of 5-20 days, administering alvelestat or a salt thereof at a dose of 120 mg twice daily for a second period of time of 5-20 days, administering alvelestat or a salt thereof at a dose of 180 mg twice daily for a third period of time of 5-20 days, and then administering alvelestat or a salt thereof at a dose of 240 mg twice daily, and wherein said disease is COPD (Chronic Obstructive Pulmonary Disease).

18. The method of claim 17, wherein said COPD is emphysema.

19. The method of claim 17, wherein said COPD is chronic bronchitis.

20. The method of claim 17 wherein said first period is 7 days, said second period is 7 days, and said third period is 7 days.

* * * * *